United States Patent
Aoyama

(10) Patent No.: US 10,991,137 B2
(45) Date of Patent: Apr. 27, 2021

(54) INFORMATION PROCESSING APPARATUS, INFORMATION PROCESSING METHOD, AND INFORMATION PROCESSING SYSTEM FOR DISPLAY OF MEDICAL IMAGES

(71) Applicant: CANON KABUSHIKI KAISHA, Tokyo (JP)

(72) Inventor: Gakuto Aoyama, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/175,971

(22) Filed: Jun. 7, 2016

(65) Prior Publication Data

US 2016/0364837 A1 Dec. 15, 2016

(30) Foreign Application Priority Data

Jun. 11, 2015 (JP) .............................. JP2015-118357
Aug. 7, 2015 (JP) .............................. JP2015-157652

(51) Int. Cl.
  *G06T 3/20* (2006.01)
  *G06T 11/60* (2006.01)
  *A61B 6/00* (2006.01)
  *A61B 6/03* (2006.01)

(52) U.S. Cl.
  CPC ............... *G06T 11/60* (2013.01); *A61B 6/032* (2013.01); *A61B 6/465* (2013.01)

(58) Field of Classification Search
  CPC ............. G06T 3/20; A61B 6/032; A61B 6/465
  USPC ......................................................... 345/677
  See application file for complete search history.

(56) References Cited

U.S. PATENT DOCUMENTS

| 5,987,345 | A | * | 11/1999 | Engelmann | G06F 19/321 |
| | | | | | 600/407 |
| 2002/0070970 | A1 | * | 6/2002 | Wood | A61B 6/032 |
| | | | | | 715/766 |
| 2004/0161139 | A1 | * | 8/2004 | Samara | G06T 15/08 |
| | | | | | 382/131 |
| 2005/0105828 | A1 | * | 5/2005 | Oosawa | A61B 6/032 |
| | | | | | 382/294 |

(Continued)

FOREIGN PATENT DOCUMENTS

| CN | 101053521 A | 10/2007 |
| CN | 102393841 A | 3/2012 |

(Continued)

OTHER PUBLICATIONS

Machine Translation of JP,2014-104099,A to English.*

*Primary Examiner* — Terrell M Robinson
(74) *Attorney, Agent, or Firm* — Canon U.S.A., Inc. I.P. Division

(57) ABSTRACT

An information processing apparatus includes a first acquiring unit, an accepting unit, a second acquiring unit, and a display control unit. The first acquiring unit acquires a processed image, wherein the processed image is acquired by processing at least one medical image. The accepting unit accepts a display instruction for the processed image based on a user's operation input. The second acquiring unit acquires information regarding a type of the processing and the medical image used for the processing. The display control unit displays the processed image, instructed by the display instruction and the medical image used for the processing, in a medical image display region based on the information regarding the type of the processing.

27 Claims, 21 Drawing Sheets

(56) References Cited

U.S. PATENT DOCUMENTS

| | | | | |
|---|---|---|---|---|
| 2006/0013462 | A1* | 1/2006 | Sadikali | G16H 40/63 |
| | | | | 382/132 |
| 2006/0033728 | A1* | 2/2006 | Sako | G16H 10/60 |
| | | | | 345/204 |
| 2006/0274885 | A1* | 12/2006 | Wang | G06Q 50/22 |
| | | | | 378/65 |
| 2010/0150418 | A1* | 6/2010 | Moriya | G06T 19/00 |
| | | | | 382/128 |
| 2010/0172474 | A1* | 7/2010 | Vogt | G06T 5/50 |
| | | | | 378/98.12 |
| 2012/0131498 | A1* | 5/2012 | Gross | G06F 17/30274 |
| | | | | 715/788 |
| 2013/0093781 | A1* | 4/2013 | Suzuki | A61B 6/461 |
| | | | | 345/581 |
| 2014/0119514 | A1 | 5/2014 | Miyazawa | |
| 2014/0313196 | A1* | 10/2014 | Mistretta | A61B 6/032 |
| | | | | 345/424 |
| 2015/0002813 | A1* | 1/2015 | Ota | A61B 3/12 |
| | | | | 351/206 |
| 2016/0247300 | A1* | 8/2016 | Takata | G06F 16/5854 |

FOREIGN PATENT DOCUMENTS

| | | |
|---|---|---|
| CN | 102573636 A | 7/2012 |
| JP | H04-117947 A | 4/1992 |
| JP | H10-155746 A | 6/1998 |
| JP | 2002-200066 A | 7/2002 |
| JP | 2004-120134 A | 4/2004 |
| JP | 2005-011121 A | 1/2005 |
| JP | 2010264254 A | 11/2010 |
| JP | 2011083591 A | 4/2011 |
| JP | 2014090743 A | 5/2014 |
| JP | 2014-104099 A | 6/2014 |
| JP | 2014104099 A * | 6/2014 |

* cited by examiner

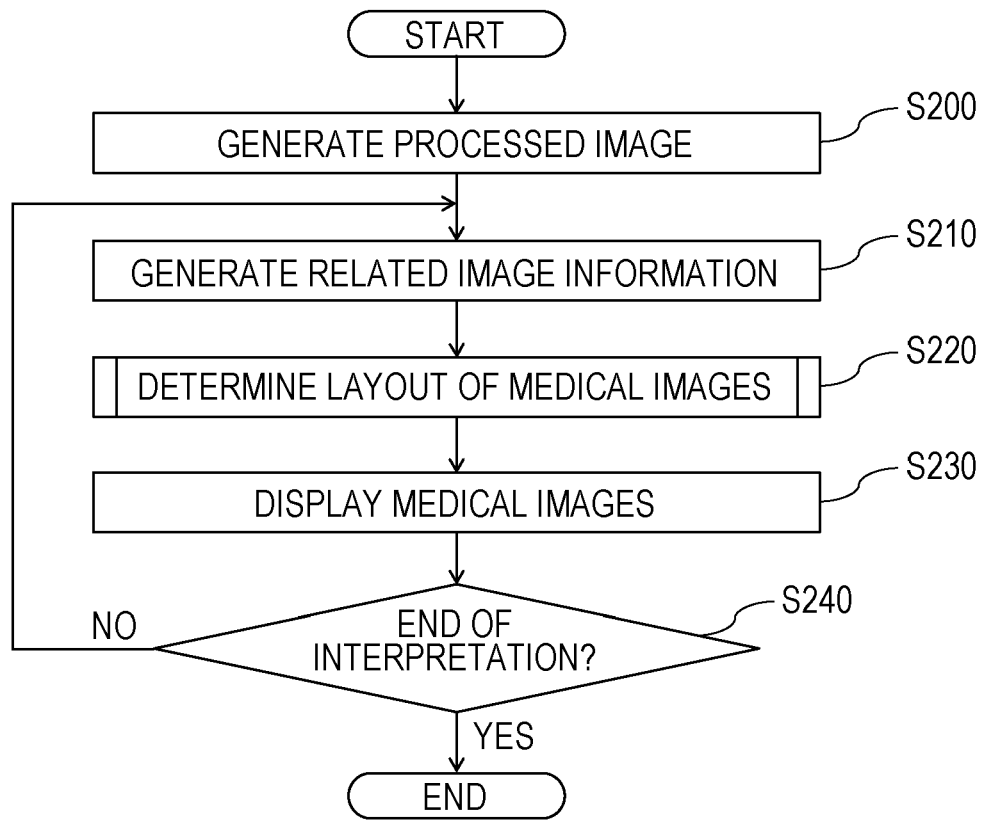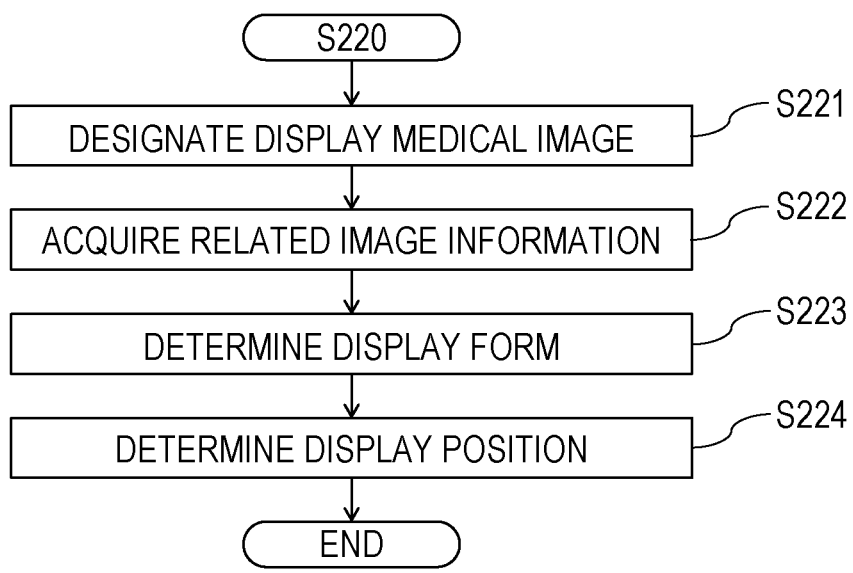

| ID | PHOTOGRAPHED DATE | MODALITY | REGION |
|---|---|---|---|
| MEDICAL IMAGE 1 | 11/11/2020 | CT | BREAST |
| MEDICAL IMAGE 2 | 11/11/2021 | CT | BREAST |
| MEDICAL IMAGE 3 | 11/11/2022 | CT | BREAST |

FIG. 7

| THUMBNAIL INFORMATION | | DISPLAY FORM | |
|---|---|---|---|
| NUMBER-OF-THUMBNAIL-ASSOCIATED IMAGE INFORMATION | TYPE-OF-THUMBNAIL-ASSOCIATED IMAGE INFORMATION | NUMBER OF ROWS (R) | NUMBER OF COLUMNS (C) |
| 3 | TEMPORAL SUBTRACTION IMAGE | 2 | 2 |
| 5 | TEMPORAL SUBTRACTION IMAGE | 2 | 3 |
| 2 | MIP IMAGE | 1 | 2 |
| 3 | MIP IMAGE | 2 | 2 |
| 2 | MIniP IMAGE | 1 | 2 |
| 3 | MIniP IMAGE | 2 | 2 |
| 3 | SUPERIMPOSED IMAGE | 2 | 2 |
| 5 | SUPERIMPOSED IMAGE | 2 | 3 |
| 1 | NULL | 1 | 1 |

FIG. 8

| THUMBNAIL INFORMATION | | DISPLAY FORM | | DISPLAY POSITION |
|---|---|---|---|---|
| NUMBER-OF-THUMBNAIL-ASSOCIATED IMAGE INFORMATION | TYPE-OF-THUMBNAIL-ASSOCIATED IMAGE INFORMATION | R | C | (Rn, Cn) |
| 3 | TEMPORAL SUBTRACTION IMAGE | 2 | 2 | (1, 1) = ORIGINAL IMAGE (FLOATING IMAGE), (1, 2) = ORIGINAL IMAGE (REFERENCE IMAGE)<br>(2, 1) = NULL, (2, 2) = TEMPORAL SUBTRACTION IMAGE |
| 5 | TEMPORAL SUBTRACTION IMAGE | 2 | 3 | (1, 1) = ORIGINAL IMAGE (FLOATING IMAGE), (1, 2) = ORIGINAL IMAGE (REFERENCE IMAGE),<br>(1, 3) = ORIGINAL IMAGE (REFERENCE IMAGE)<br>(2, 1) = NULL, (2, 2) = TEMPORAL SUBTRACTION IMAGE, (2, 3) = TEMPORAL SUBTRACTION IMAGE |
| 2 | MIP IMAGE | 1 | 2 | (1, 1) = ORIGINAL IMAGE, (1, 2) = MIP IMAGE |
| 3 | MIP IMAGE | 2 | 2 | (1, 1) = ORIGINAL IMAGE, (1, 2) = MIP IMAGE<br>(2, 1) = NULL, (2, 2) = MIP IMAGE |
| 2 | MInIP IMAGE | 1 | 2 | (1, 1) = ORIGINAL IMAGE, (1, 2) = MInIP IMAGE |
| 3 | MInIP IMAGE | 2 | 2 | (1, 1) = ORIGINAL IMAGE, (1, 2) = MInIP IMAGE<br>(2, 1) = NULL, (2, 2) = MInIP IMAGE |
| 3 | SUPERIMPOSED IMAGE | 2 | 2 | (1,1) = ORIGINAL IMAGE (BASE IMAGE), (1, 2) = ORIGINAL IMAGE (LAYER IMAGE)<br>(2, 1) = NULL, (2, 2) = SUPERIMPOSED IMAGE |
| 5 | SUPERIMPOSED IMAGE | 2 | 3 | (1,1) = ORIGINAL IMAGE (BASE IMAGE), (1, 2) = ORIGINAL IMAGE (LAYER IMAGE),<br>(1,3) = ORIGINAL IMAGE (LAYER IMAGE)<br>(2,1) = NULL, (2, 2) = SUPERIMPOSED IMAGE, (2, 3) = SUPERIMPOSED IMAGE |
| 1 | NULL | 1 | 1 | (1, 1) = ORIGINAL IMAGE |

FIG. 19

| TYPE-OF-THUMBNAIL-ASSOCIATED IMAGE INFORMATION | DISPLAY FORM | |
|---|---|---|
| | NUMBER OF ROWS (R) | NUMBER OF COLUMNS (C) |
| TEMPORAL SUBTRACTION IMAGE | HIGHEST NUMBER OF NUMBERS OF DIFFERENT TEMPORAL SUBTRACTION IMAGES CORRESPONDING TO REFERENCE IMAGES + 1 | TOTAL NUMBER OF DIFFERENT ORIGINAL IMAGES |
| MIP IMAGE | TOTAL NUMBER OF DIFFERENT PROCESSED IMAGES | FIXED VALUE : 2 |
| MInIP IMAGE | TOTAL NUMBER OF DIFFERENT PROCESSED IMAGES | FIXED VALUE : 2 |
| SUPERIMPOSED IMAGE | HIGHEST NUMBER OF NUMBERS OF DIFFERENT SUPERIMPOSED IMAGES CORRESPONDING TO LAYER IMAGES | TOTAL NUMBER OF DIFFERENT ORIGINAL IMAGES |

FIG. 20

| TYPE-OF-THUMBNAIL-ASSOCIATED IMAGE INFORMATION | DISPLAY POSITION |
|---|---|
| TEMPORAL SUBTRACTION IMAGES | ARRANGED IN THE FOLLOWING PRIORITY ORDER:<br>a. ORIGINAL IMAGE (FLOATING IMAGE, REFERENCE IMAGE) IS ARRANGED ON FIRST ROW<br>b. ARRANGED CHRONOLOGICALLY WITH RESPECT TO THE PHOTOGRAPHED DATE OF ORIGINAL IMAGE IN REGIONS HAVING COLUMN NUMBERS IN INCREASING ORDER OF THE FIRST ROW<br>c. TEMPORAL SUBTRACTION IMAGES ARE ARRANGED ON THE SECOND AND SUBSEQUENT ROWS<br>d. TEMPORAL SUBTRACTION IMAGES ARE ARRANGED IN REGIONS HAVING THE SAME COLUMN NUMBER AS THE CORRESPONDING REFERENCE IMAGE<br>e. TEMPORAL SUBTRACTION IMAGES ARE ARRANGED IN ORDER FROM THE PHOTOGRAPHED DATE OF ITS FLOATING IMAGE CLOSEST TO THE PHOTOGRAPHED DATE OF REFERENCE IMAGE IN REGIONS IN INCREASING ORDER OF ROW NUMBERS |
| MIP IMAGES | ARRANGED IN THE FOLLOWING PRIORITY ORDER:<br>a. ORIGINAL IMAGE IS ARRANGED ON FIRST COLUMN<br>b. MIP IMAGE IS ARRANGED ON SECOND COLUMN<br>c. MIP IMAGES ON SECOND COLUMN ARE ARRANGED CHRONOLOGICALLY WITH RESPECT TO GENERATED DATA AND TIME |
| MInIP IMAGES | ARRANGED IN THE FOLLOWING PRIORITY ORDER:<br>a. ORIGINAL IMAGE IS ARRANGED ON FIRST COLUMN<br>b. MInIP IMAGE IS ARRANGED ON SECOND COLUMN<br>c. MInIP IMAGES ON SECOND COLUMN ARE ARRANGED CHRONOLOGICALLY WITH RESPECT TO GENERATED DATA AND TIME |
| SUPERIMPOSED IMAGE | ARRANGED IN THE FOLLOWING PRIORITY ORDER:<br>a. ORIGINAL IMAGE (BASE IMAGE, LAYER IMAGE) IS ARRANGED ON FIRST ROW<br>b. ARRANGED CHRONOLOGICALLY WITH RESPECT TO THE PHOTOGRAPHED DATE OF ORIGINAL IMAGE IN REGIONS HAVING COLUMN NUMBERS IN INCREASING ORDER OF THE FIRST ROW<br>c. SUPERIMPOSED IMAGES ARE ARRANGED ON THE SECOND AND SUBSEQUENT ROWS<br>d. SUPERIMPOSED IMAGES ARE ARRANGED IN REGIONS HAVING THE SAME COLUMN NUMBER AS THE CORRESPONDING LAYER IMAGE<br>e. SUPERIMPOSED IMAGES ARE ARRANGED CHRONOLOGICALLY WITH RESPECT TO GENERATED DATES AND TIMES OF SUPERIMPOSED IMAGES IN REGIONS IN INCREASING ORDER OR ROW NUMBERS |

INFORMATION PROCESSING APPARATUS, INFORMATION PROCESSING METHOD, AND INFORMATION PROCESSING SYSTEM FOR DISPLAY OF MEDICAL IMAGES

BACKGROUND OF THE INVENTION

Field of the Invention

The present invention relates to an information processing apparatus, an information processing method, and an information processing system.

Description of the Related Art

A wide variety of medical images has been applied for medical examinations and treatments, and processed images acquired by performing further image processing on medical images subject to medical examinations and treatments have also been used very often. For such medical examinations and treatments, a processed image generated as described above and a plurality of medical images associated therewith are displayed on a medical image display apparatus. In a case where a plurality of medical images including a processed image are compared to execute a medical examination and treatment, the medical images may be displayed in an appropriate display form on a corresponding display region of the medical image display apparatus.

Japanese Patent Laid-Open No. 2014-104099 discloses that, in response to an operation for selecting a preview image corresponding to a medical image and moving it to a template region, the medical image is displayed in a layout based on the template.

For displaying a plurality of related medical images at target positions in a display region, the selecting operation for display must be performed for each of the plurality of medical images. This operation may possibly require user's time and effort.

SUMMARY OF THE INVENTION

According to some embodiments of the present invention, an information processing apparatus includes a first acquiring unit configured to acquire a processed image, wherein the processed image is acquired by processing at least one medical image, an accepting unit configured to accept a display instruction for the processed image based on a user's operation input, a second acquiring unit configured to acquire information regarding a type of the processing and the medical image used for the processing, and a display control unit configured to display the processed image, instructed by the display instruction and the medical image used for the processing, in a medical image display region based on the information regarding the type of the processing.

A medical image to be displayed in a medical image display region is designated, and related image information being information regarding an image associated with the designated medical image is acquired. Based on the related image information, the position where the medical image is to be arranged in the medical image display region is determined. Further features of the present invention will become apparent from the following description of exemplary embodiments with reference to the attached drawings.

BRIEF DESCRIPTION OF THE DRAWINGS

FIGS. 2A and 2B are flowcharts illustrating processes according to the first embodiment.

FIG. 7 illustrates correspondence examples between related image information and display forms.

FIG. 8 illustrates correspondence examples among display forms, related image information, and display positions.

FIG. 19 illustrates a correspondence example between processed-image type information and display forms under a specific condition.

FIG. 20 illustrates a correspondence example between processed-image type information and display positions under a specific condition.

DESCRIPTION OF THE EMBODIMENTS

Embodiments of the present invention will be described with reference to drawings.

Figure 1:
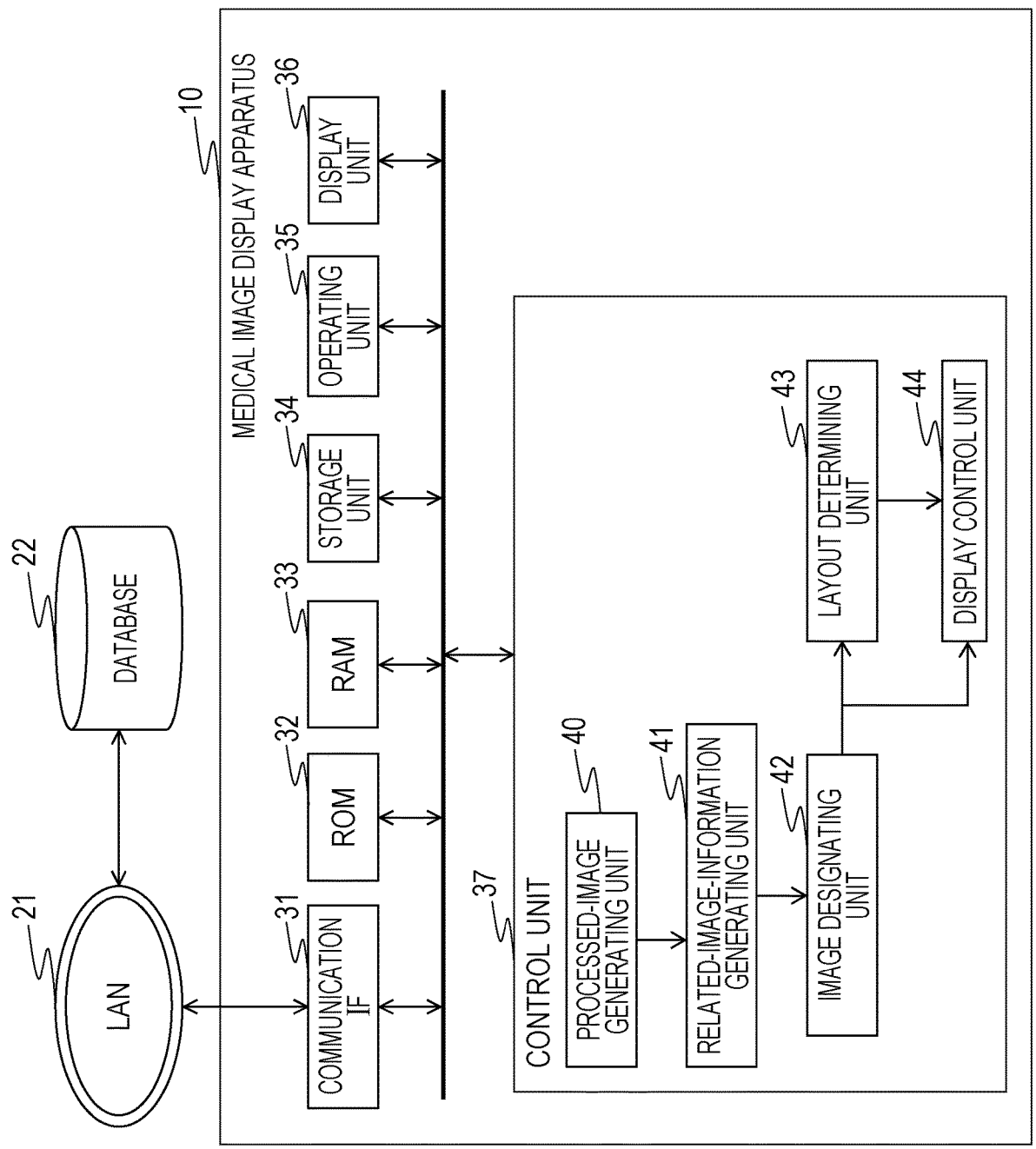
FIG. 1 is a block diagram illustrating a medical image display system according to a first embodiment.

FIG. 1 is a block diagram illustrating a medical image display system according to a first embodiment of the present invention. The medical image display system includes a medical image display apparatus 10 (hereinafter, called a display apparatus 10) and a database 22. The display apparatus 10 and the database 22 are connected mutually communicably through a communication unit. According to this embodiment, the communication unit may be a local area network (LAN) 21.

The database 22 manages examination information such as medical images. The display apparatus 10 acquires a medical image managed by the database 22 over the LAN 21. The database 22 may be a Picture Archiving and Communication System (PACS) server, for example.

The display apparatus 10 includes, as its functional components, a communication IF 31, a ROM 32, a RAM 33, a storage unit 34, an operating unit 35, a display unit 36, and a control unit 37.

The communication interface (IF) 31 may be implemented by a LAN card, for example, and is responsible for communication between an external device such as the database 22 and the display apparatus 10 over the LAN 21. The ROM (read only memory) 32 may be implemented by a non-volatile memory and stores a program. The RAM (random access memory) 33 may be implemented by a volatile memory and may temporarily store information. The storage unit 34 may be implemented by a hard disk drive (HDD) and stores information. The operating unit 35 may be implemented by a keyboard and a mouse, for example, and may input an instruction from a user to the control unit 37. The display unit 36 may be implemented by a display device, for example, and may display information. The control unit 37 may be implemented by a CPU (central processing unit), for example, and may generally control processes in the display apparatus 10. The control unit 37 has, as its functional components, a processed-image generating unit 40, a related-image-information generating unit 41, an image designating unit 42, a layout determining unit 43, and a display control unit 44. The components of the control unit 37 cause the CPU to execute programs for corresponding functions.

The processed-image generating unit 40 generates a processed image in accordance with an operation input. First of all, at least one medical image designated by the image designating unit 42 is read out from the database 22 and is saved in the storage unit 34. Next, the readout medical image undergoes an image process, and at least one processed image can thus be generated. The processed image acquired by performing an image process on a medical image may be an maximum intensity projection or MIP image generated by maximum intensity projection (MIP), for example. A maximum intensity projection image or MIP image is acquired by displaying the highest value in a projection path in an arbitrary view direction of a three-dimensional image on a plane of projection. Another processed image example is a temporal subtraction image generated by performing registration processing and image difference processing on a plurality of temporally different medical images. Another processed image example may be a MInip image generated by minimum intensity projection (MInip). A minimum intensity projection image or a MInip image is generated by displaying the lowest value in a projection path in an arbitrary view direction of a three-dimensional image to a plane of projection. Another example may be a superimposed image generated by superimposition processing using a plane on a plurality of different medical images. The superimposed image can be acquired by superimposing a plurality of different medical image on a display screen. Then, at least one of generated processed images is saved in the storage unit 34. Processed image information is also generated, is stored in the storage unit 34 or RAM 33 in association with the corresponding processed image, and is output to the related-image-information generating unit 41. The processed image information will be specifically described below. Such a processed image acquired by performing an image process on a medical image is also handled as a medical image. The term "processed image" refers to an image acquired by performing an image process on one or more medical images subject to a diagnosis. The term "medical image subject to a diagnosis" refers to an image acquired by performing a publicly known image process on image data acquired by an apparatus configured to capture a medical image so as to acquire a medical image suitable for a diagnosis. For example, a Computed Tomography (CT) apparatus irradiates an X-ray to an object by changing the angle of the X ray around the object to acquire a one-dimensional distribution of relative X-ray absorption coefficients called CT values as image data. After that, a process called image reconstruction is performed on the image data to acquire an X-ray absorption coefficient of each of pixels of a target multi-planar reconstruction (MPR) image, and a medical image called a tomographic image is thus acquired. The term "processed image" refers to a temporal subtraction image generated by performing registration processing and image difference processing on a plurality of tomographic images at different time points during image acquisition processing performed by a CT apparatus.

The related-image-information generating unit 41 generates a thumbnail of a medical image used for generating a processed image and a thumbnail of the generated processed image and related image information regarding the thumbnails. The related image information will be specifically described below. Then, the thumbnails and the related image information are associated with each other. The generated thumbnails are arranged in a thumbnail display region of a medical image display apparatus through the display control unit 44 and are displayed on the display unit 36. The generated related image information is output to the layout determining unit 43 and display control unit 44 through the storage unit 34 or the RAM 33.

The image designating unit 42 designates a medical image to be observed in accordance with a user's operation input. First of all, a user may select a medical image to be observed for display by performing an operation input on the corresponding thumbnail by using the operating unit 35, for example. How the operation input is performed for the selection will be specifically described below. The image designating unit 42 in response to the operation input for the selection outputs related image information regarding the designated medical image to the layout determining unit 43. As another example, in response to an operation input for selecting a medical image used for generating a processed image in the processed-image generating unit 40, the image designating unit 42 may designate both of the medical image and a processed image generated by the processed-image generating unit 40 in response to the operation.

The layout determining unit 43 acquires related image information corresponding to the medical image designated by the image designating unit 42. In other words, the related image information associated with the thumbnail selected by a user is acquired. Based on the acquired related image information, the layout on a medical image display region of the medical image designated by the image designating unit 42 and a medical image related to the medical image is determined. The determined layout is then output to the display control unit 44.

The display control unit 44 uses the related image information generated by the related-image-information generating unit 41 to acquire the medical image designated by the image designating unit 42 and a medical image related to the medical image from the database 22 through the communication IF 31 and the LAN 21. All of the acquired medical images are arranged on the medical image display region in accordance with the layout determined by the layout determining unit 43 and are displayed on the display unit 36.

As another example, a case will be described in which a processed image is generated and is stored in the database 22 in advance. The information regarding a medical image used for generating the processed image is stored within a DICOM header if the processed image is generated under DICOM (digital imaging and communications in medicine)

rules. The information may be stored as a separate file in association with the processed image. In this case, the image designating unit 42 in response to an operation input for selecting a medical image to be observed designates the medical image stored in the database 22 through the communication IF 31. The layout determining unit 43 may acquire the related image information from data stored in the DICOM header, for example, and determine the layout on the medical image display region of the medical image and a medical image related thereto. For example, when one processed image is designated by the image designating unit 42, the layout determining unit 43 acquires information regarding the original image stored within the DICOM header, that is, the related image information. Based on the acquired related image information, the layout of the processed image and medical image related thereto is determined by the layout determining unit 43. In accordance with the determined layout, the processed image and the related medical image are displayed on the display unit 36 through the display control unit 44.

It should be noted that at least some of the components of the control unit 37 may be implemented as independent devices. At least some of the components may be implemented by software which implements functionalities of the components. In this case, the software for implementing the functionalities may operate on a server over a network such as a cloud network. For example, the functionalities of the components included in the control unit 37 as illustrated in FIG. 1 may be implemented on the database 22 being a PACS server. The display control unit 44 displays operations to be executed on the PACS server on a monitor of a computer (not illustrated). When an operation relating to generation of a processed image is input through the computer and in response to the operation input through the communication IF, processing to be executed by the processed-image generating unit 40 and processing to be executed by the related-image-information generating unit 41 are executed. When an operation for selecting a medical image to be displayed is input through the computer, the image designating unit 42 in response to the operation input received through the communication IF designates the medical image. The processing to be executed by the layout determining unit 43 is then executed to determine the layout of the medical image and a medical image related thereto. The determined layout is output as data displayable by a monitor of the computer through the display control unit 44.

The following embodiment assumes that the components are implemented by software in a local environment.

Next, an overall processing procedure to be executed by the control unit 37 according to the first embodiment of the present invention will be described. FIGS. 2A and 2B are flowcharts illustrating processing according to the first embodiment and to be executed by the control unit 37.

In step S200, the processed-image generating unit 40 reads out a medical image selected by a user from the database 22 and saves it in the storage unit 34. Next, the processed-image generating unit 40 performs an image process based on the operation input on the read medical image to generate at least one processed image. The processed-image generating unit 40 saves the at least one generated processed image in the storage unit 34. The processed-image generating unit 40 generates processed image information and saves it in association with the processed image in the storage unit 34 or the RAM 33. The processed image information here includes the following five information pieces. A first information piece (hereinafter, called the number-of-processed-images information) is information describing the number of processed images generated by the image process. A second information piece (hereinafter, called processed-image storage-location information) is information describing storage locations of all processed images generated by the image process. The processed-image storage-location information describes a storage destination path in the storage unit 34 of the processed image, for example. A third information piece (hereinafter, called the number-of-original-images information) is information describing the number of medical images used for generating the processed image (hereinafter, called an original image). A fourth information piece (hereinafter, called original-image storage-location information) is information describing storage locations of all original images. The original-image storage-location information here describes a storage destination path in the storage unit 34 of the original image, for example. A fifth information piece (hereinafter, called processed-image type information) is information by which the type of the processed image is identified. In a case where a plurality of processed images is generated by the image process, the processed-image generating unit 40 generates and saves the processed-image type information for each of the processed images. The processed-image type information may be "temporal subtraction image" or "MIP image", for example. The processed-image type, "temporal subtraction image", refers to a processed image generated by performing a deformable registration process and an image difference process on two medical images acquired by normally photographing one identical object at two different time points. The processed-image type, "MIP image", refers to a processed image generated by performing maximum intensity projection which is a publicly known technology on a medical image. The processed image information may include information from which the five information piece as described above can be acquired. For example, the number-of-original-images information can be acquired from processed image information including the fourth information piece which is original-image storage-location information, without the third information piece which is the number-of-original-images information.

The processing in step S200 will be described more specifically. In response to a user's operation input, a medical image M103 acquired by photographing one object by using a CT apparatus on Nov. 11, 2020 and a medical image M104 acquired by photographing the same object by using the CT apparatus on Nov. 11, 2021 are read out from the database 22 and are saved in the storage unit 34. Next, in response to a user's operation input, a deformable registration process and an image difference process which are publicly known technologies are performed on the medical image M103 and the medical image M104 to generate a temporal subtraction image M105 which is then saved in the storage unit 34. The corresponding processed image information is generated and is saved in the storage unit 34 or the RAM 33. In this example, the processed image information includes the following details. Because one processed image, the temporal subtraction image M105, has been generated, the number-of-processed-images information is "1". The processed-image storage-location information describes a storage destination path in the storage unit 34 of the temporal subtraction image M105. Because two original images, the medical image M103 and the medical image M104, have been used for generating the processed image, the number-of-original-images information is "2". The original-image storage-location information is storage destination paths in the storage unit 34 of the two medical images, medical image M103 and medical image M104. The processed-image type information is "temporal subtraction image".

In another example, in response to a user's operation input, the medical image M103 photographed by a CT apparatus in Nov. 11, 2020 of one object is read out from the database 22 and is saved in the storage unit 34. Next, in response to a user's operation input, maximum intensity projection is performed on the medical image M103 to generate an MIP image M106 which is then saved in the storage unit 34. The corresponding processed image information is generated and is saved in the storage unit 34 or the RAM 33. In this example, the processed image information has the following details. Because one processed image, MIP image M106, has been generated, the number-of-processed-images information is "1". The processed-image storage-location information describes the storage destination paths in the storage unit 34 of the MIP image M106. Because one original image, medical image M103, has been used for generating the processed image, the number-of-original-images information is "1". The original-image storage-location information describes the storage destination path in the storage unit 34 of the medical image M103. The processed-image type information is "MIP image".

In step S210, the related-image-information generating unit 41 reads out a medical image selected by a user and a processed image from the database 22 or the storage unit 34. Reduced images being examples of thumbnails of the medical image and processed image are generated. The thumbnail generation is performed by a publicly known technology. The medical images are associated with the generated thumbnails under a predetermined rule (hereinafter, called a thumbnail rule). Concrete examples of the thumbnail rule may be "the processed image and all original images are associated with the thumbnail of the processed image", and "the medical image is only associated with the thumbnails of medical images other than the processed image".

Next, related image information regarding the generated thumbnails is generated. The related image information here includes the following three information pieces. A first information piece is information describing the number of medical images (including processed images) associated with a thumbnail (hereinafter, called number-of-thumbnail-associated image information). Under the concrete example of the thumbnail rule, for example, processed images and all original images are associated with thumbnails of the processed images. Thus, the number-of-thumbnail-associated image information describes a sum of the number of the processed images and the number of all original images of the processed images. This information can be acquired by calculating the sum with reference to the number-of-processed-images information in the processed image information of the processed images generated in step S200 and the number-of-original-images information. Under the concrete example of the thumbnail rule, the thumbnail of a medical image other than the processed images is only associated with the medical image. Thus, the number-of-thumbnail-associated image information is "1". A second information piece is information describing the type of a medical image associated with a thumbnail (hereinafter, called type-of-thumbnail-associated image information). Here, the type-of-thumbnail-associated image information of a thumbnail for a processed image is the processed-image type information of the processed image and can be acquired with reference to the processed-image type information of the processed image generated in step S200. The type-of-thumbnail-associated image information of a thumbnail for a medical image excluding processed images is NULL. A third information piece is information describing storage locations of all medical images associated with thumbnails (hereinafter, called thumbnail-associated image storage location information). The thumbnail-associated image storage location information for thumbnails of processed images here can be acquired with reference to processed-image storage-location information in the processed image information of the processed images generated in step S200 and the original-image storage-location information. The thumbnail-associated image storage location information regarding a thumbnail of a medical image other than the processed image can be acquired as a storage destination path in the database 22 or the storage unit 34 of the medical image. In other words, the related image information of a processed image includes information describing the number of medical images used for generating the processed image and the type of image processing. The second information piece and the third information piece may only be acquired as the related image information, and the number of medical images used for generating the processed image may be acquired based on the thumbnail-associated image storage location information which is the third information piece. In this case, the thumbnail-associated image storage location information functions as the information describing the number of medical images used for generating the processed image.

The processed image information and the related image information have been described above. The "image related to a medical image" may be an image acquired based on the processed image information, for example. In other words, the "images related to a medical image" may include the medical image itself and medical images used for generating a processed image if the medical image is the processed image. The "information regarding images related to a medical image" may be the related image information, for example.

Figures 6A, 6B:
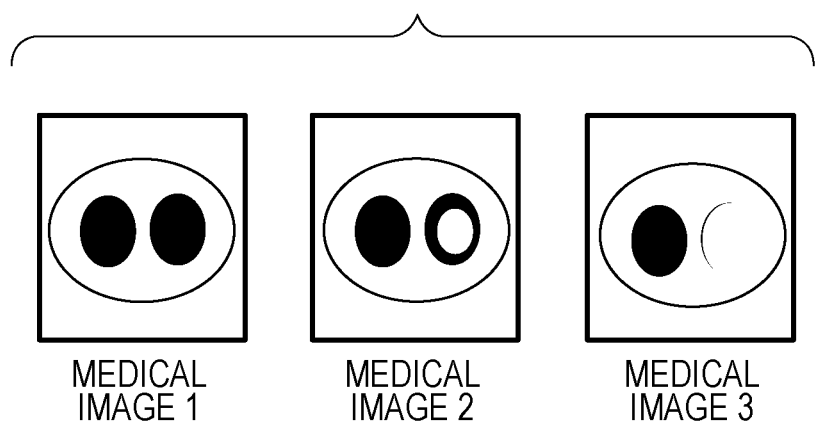
FIGS. 6A and 6B illustrate thumbnail examples.

Next, the generated reduced images being thumbnails are displayed on the display unit 36 in the medical image display apparatus, and the generated related image information is stored in association with the reduced images in the storage unit 34 or the RAM 33. According to this embodiment, the thumbnail is representative of information associated with a corresponding medical image when list of information pieces regarding many medical images are displayed. More specifically, for example, a character string in a list of character strings corresponding to medical images, as illustrated in FIG. 6A, and a reduced image corresponding to a medical image may be a thumbnail, as illustrated in FIG. 6B. The thumbnails may have any forms if a list of information pieces corresponding to a plurality of medical images can be displayed. In the following description, a thumbnail is a reduced image corresponding to a medical image, as illustrated in FIG. 6B according to this embodiment. The illustrated form will generally be called a thumbnail below.

Next, the processing in step S210 will be described more specifically. In response to a user's operation input, the related-image-information generating unit 41 reads out the medical image M103 from the storage unit 34 and generates a thumbnail 103 for the medical image M103. The related-image-information generating unit 41 also reads out a medical image M104 from the storage unit 34 and generates a thumbnail 104 for the medical image M104. The related-image-information generating unit 41 further reads out the temporal subtraction image M105 from the storage unit 34 and generates a thumbnail 105 for the temporal subtraction image M105. Next, it is assumed that the thumbnail rules according to this embodiment are "a thumbnail for the processed image is associated with not only the processed image but also all original images" and "the thumbnail for a medical image other than the processed image is only associated with the medical image". Under the thumbnail rules, a medical image is associated with its corresponding thumbnail. In other words, the medical image M103 is associated with the thumbnail 103. The medical image M104 is associated with the thumbnail 104. The temporal subtraction image M105, the medical image M103, and the medical image M104 are associated with the thumbnail 105. The related image information regarding each of the thumbnails is generated. The number-of-thumbnail-associated image information regarding the thumbnail 103 is "1", and the type-of-thumbnail-associated image information is NULL, and the thumbnail-associated image storage location information is the storage destination path in the storage unit 34 of the medical image M103. The number-of-thumbnail-associated image information regarding the thumbnail 104 is "1", the type-of-thumbnail-associated image information is NULL, and the thumbnail-associated image storage location information is the storage destination path in the storage unit 34 of the medical image M104. Regarding the thumbnail 105, with reference to the processed image information regarding the temporal subtraction image M105 generated in step S200, the number-of-processed-images information is "1", the number-of-original-images information is "2", and the number-of-thumbnail-associated image information is "3". Also, with reference to the processed-image type information regarding the temporal subtraction image M105 generated in step S200, the type-of-thumbnail-associated image information is "temporal subtraction image". The thumbnail-associated image storage location information can be acquired with reference to the processed-image storage-location information generated in step S200 and the original-image storage-location information. In other words, the thumbnail-associated image storage location information describes the storage destination paths in the storage unit 34 of the temporal subtraction image M105, the medical image M103, and the medical image M104. In other words, related image information is information regarding an image associated with a medical image. The related image information is stored in association with the thumbnail corresponding to the medical image. From another point of view, the related image information is information associated with the thumbnail corresponding to the medical image. Next, the generated thumbnail 103, thumbnail 104 and thumbnail 105 are displayed on the display unit 36 of the display apparatus 10, and the generated related image information is stored in the storage unit 34 in association with the thumbnails.

Figure 3:
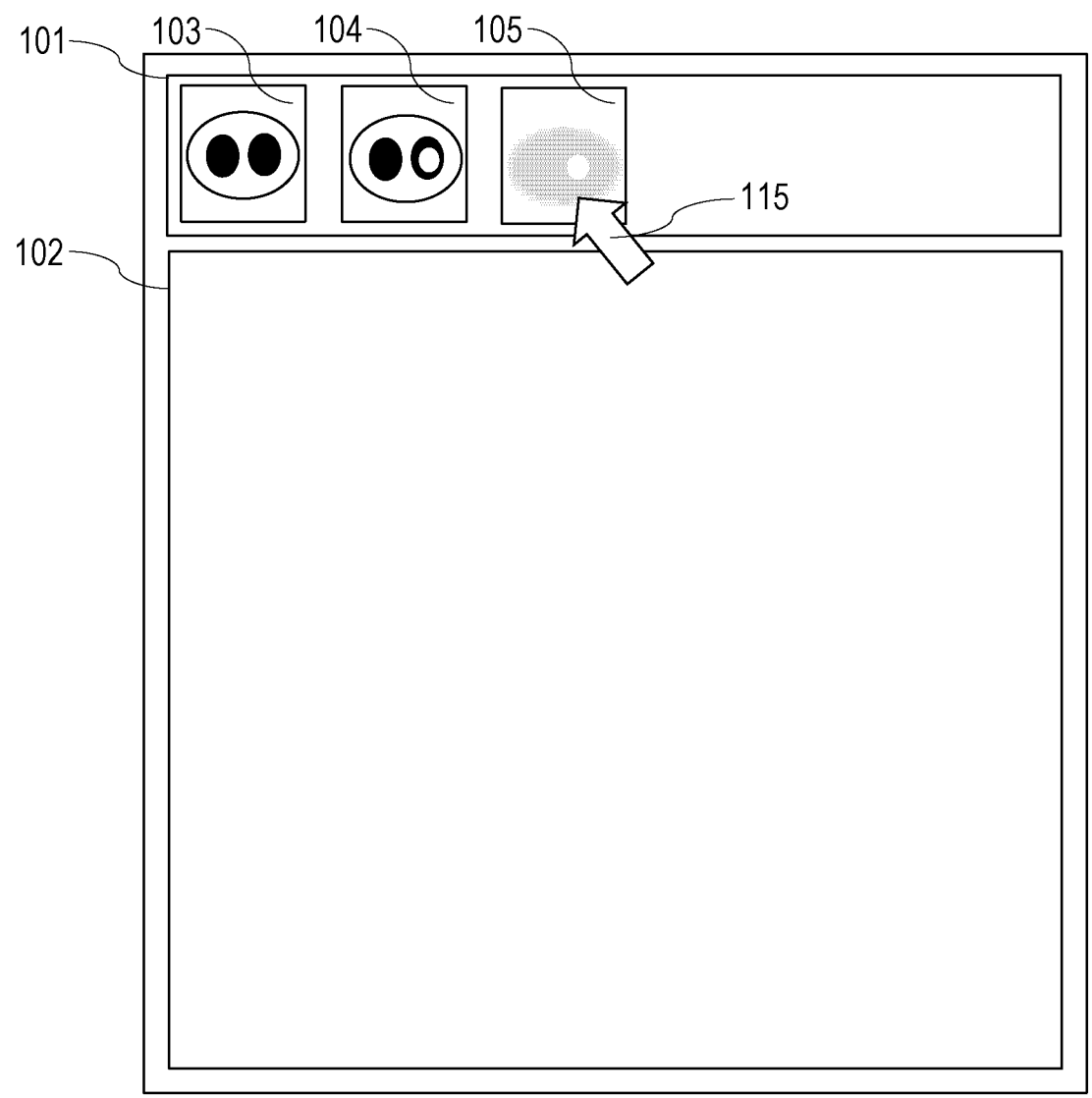
FIG. 3 illustrates a first example of a displayed screen in a process according to the first embodiment.

FIG. 3 illustrates a screen example displayed on the display unit 36 when the processing in step S210 completes. Referring to FIG. 3, a region 101 is representative of a thumbnail display region. The thumbnail display region displays thumbnails of past and present medical images of one object or a processed image acquired by processing them as original images. The thumbnail 103, the thumbnail 104, and the thumbnail 105 are displayed in the region in FIG. 3. A region 102 is representative of a medical image display region. The medical image display region displays a medical image to be interpreted by a user or a medical image being reference information for radiogram interpretation. Based on the medical images displayed in the medical image display region, a user can execute various functions of the medical image display apparatus on the displayed medical images. For example, the display apparatus 10 according to this embodiment has functions such as a function for enlarging/reducing the size of a whole medical image, a function for translating a display position, a figure drawing function, and a gray-level measuring function. In the display apparatus 10 according to this embodiment, the display region can be divided into a plurality of regions, and different medical images can be displayed in the plurality of division regions simultaneously. The illustrated arrow 115 may be representative of a mouse pointer, for example, and the tip position of the arrow indicates the current position of an input performed through the operating unit 35.

In step S220, the layout determining unit 43 determines a layout on the medical image display region of medical images associated with a thumbnail selected by a user through the operating unit 35 in accordance with the flowchart in FIG. 2B.

In step S221, the medical image corresponding to the thumbnail selected by the user is designated as a medical image to be displayed in the medical image display region.

In step S222, the related image information generated in step S210 is acquired for the thumbnail selected by the user. In other words, related image information corresponding to the medical image designated in step S221 is acquired.

Figure 4A:
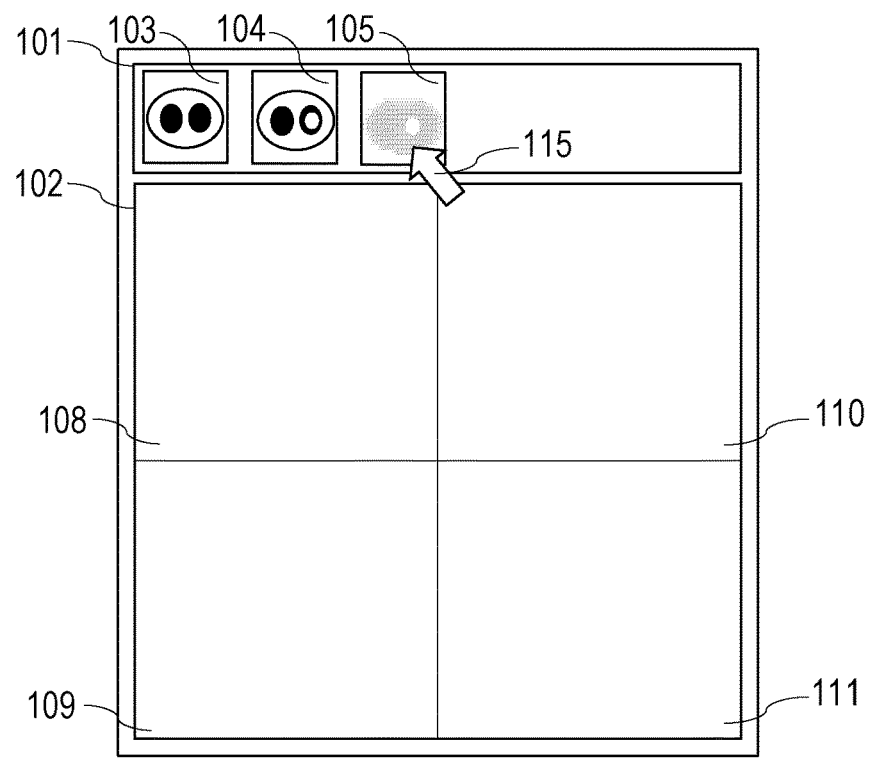
FIGS. 4A and 4B illustrate examples in which a medical image display region is divided into a plurality of regions.
Figure 4B:
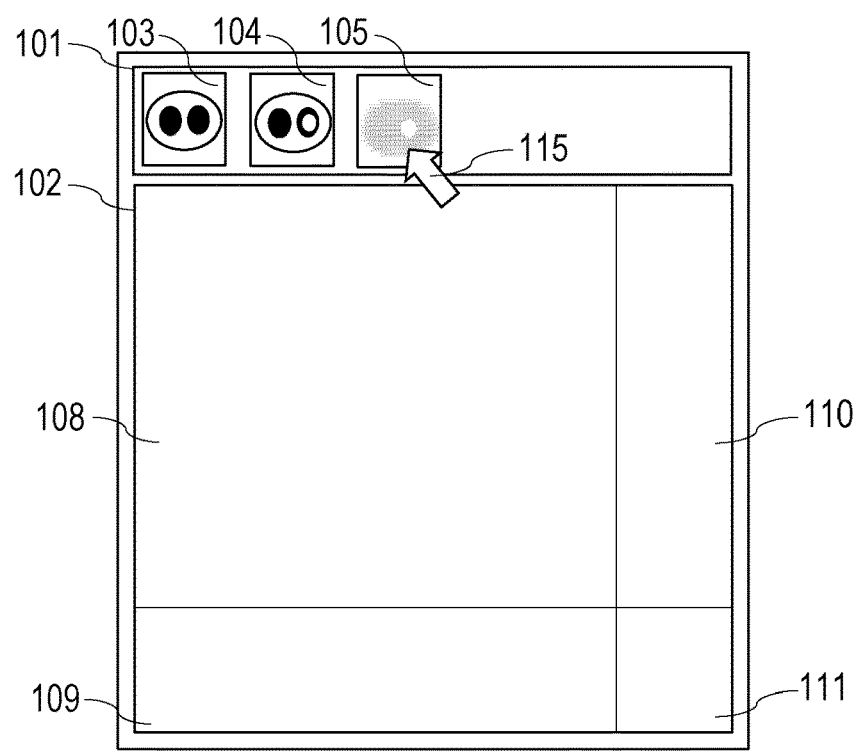

In step S223, the display form of the medical image display region is set based on the related image information acquired in step S222. Here, correspondences between related image information and display forms may be preset, and a display form corresponding to the acquired related image information is set. FIG. 7 illustrates example correspondences between related image information and display forms. FIG. 7 has R indicating a number of rows (R≥1) for dividing the medical image display region and C indicating a number of columns (C≥1) for dividing the medical image display region. The correspondence relation may be set by a user in advance and may be changed as required while the user is using the medical image display system. FIGS. 4A and 4B illustrate an example of a medical image display region divided into a plurality of regions where R=2 and C=2 are set. In this case, the display form is set such that the medical image display region 102 can be divided into four regions of regions 108, 109, 110, and 111. According to another display form setting method, the sizes of division regions may also be changed at the same time. For example, as illustrated in FIG. 4B, the display form may be set such that the size of the region 108 can be enlarged and that the size of the region 111 can be reduced.

In step S224, based on the display form set in step S223 and the related image information acquired in step S222, the display positions of medical images corresponding to the thumbnails are determined. Correspondences among display forms, related image information, and display positions may be preset, and display positions are determined based on the set correspondences. FIG. 8 illustrates example correspondences among display forms, related image information, and display positions. FIG. 8 has Rn indicating a row number and Cn indicating a column number. For example, in a case where (Rn, Cn) is (1, 2), it may indicate the region 110 in FIGS. 4A and 4B which is a region at a position of the first row and the second column in the medical image display region, for example. Each of the equal signs in FIG. 8 represents that an image of a type given on the right side is displayed in a region at a position designated on the left side. However, "NULL" on the right side means that nothing is displayed in a region at a position designated on the left side. It is assumed here that the correspondence relation may be set by a user in advance. For example, for easy comparison and radiogram interpretation by a user, a floating image of temporal subtraction images and a reference image may be aligned horizontally on a displayed screen. A reference image and a temporal subtraction image at an identical position on an image of an anatomical structure are aligned vertically on a display screen. For that, a correspondence relation satisfying conditions "a floating image and a reference image are arranged on an identical row" and "a reference image and a temporal subtraction image are arranged on an identical column" may be preset. It may be configured such that the correspondence relation may be changed as required while a user is using the medical image display system. In other words, a medical image display region is divided based on the related image information, and a layout is determined such that medical images can be displayed in the division regions.

The floating images, reference images, base images, and layer images illustrated in FIG. 8 will be described below. When a temporal subtraction image is generated as a processed image, a medical image to be referred for registration in a deformable registration process is called a reference image, and a medical image to undergo registration toward the reference image is called a floating image. When a superimposed image is generated as a processed image, a medical image being a base of a superimposition process using an plane is called a base image, and a medical image to be superimposed on the base image is called a layer image. According to this embodiment, the reference image to the temporal subtraction image M105 is the medical image M104, and the medical image M103 is a floating image.

The processing in step S220 will be described more specifically. A case will be described in which a user selects the thumbnail 105. First, in step S221, the image designating unit 42 in response to a user's operation input for selecting the thumbnail 105 designates the medical image M105 as a medical image to be displayed in a medical image display region. In step S222, the layout determining unit 43 acquires related image information associated with the thumbnail 105. In other words, "3" as the number-of-thumbnail-associated image information and "temporal subtraction image" as the type-of-thumbnail-associated image information are acquired. In step S223, referring to FIG. 7, a display form is set based on the display form R=2 and C=2 corresponding to the related image information. In other words, the medical image display region 102 is divided so as to have two rows and two columns. In step S224, based on the correspondence relation illustrated in FIG. 8, it is determined to arrange the original image being a floating image at a position of Rn=1, Cn=1 or the region 108. It is determined that an original image being a reference image is arranged at a position, of Rn=1, Cn=2 or the region 110, and a temporal subtraction image is arranged at a position of Rn=2, Cn=2 or the region 111. As described above, the medical image display region is divided in gridlike fashion based on the number of rows and the number of columns, and medical images are arranged on the divided regions (or division regions).

In a case where a user selects a medical image which is not a processed image, for example, in a case where the thumbnail 104 is selected, the layout determining unit 43 acquires related image information associated with the thumbnail 104. "1" as the number-of-thumbnail-associated image information and "NULL" as the type-of-thumbnail-associated image information are acquired. In this case, because the number-of-thumbnail-associated image information is "1", it is determined that the medical image display region 102 is not to be divided and the medical image M104 is arranged on the medical image display region 102.

In step S230, the display control unit 44 reads out a medical image corresponding to the medical image designated in step S220 from the database 22 or the storage unit 34 based on the thumbnail-associated image storage location information. Then, the read out medical image is arranged in the medical image display region in accordance with the layout determined in step S220 and is displayed by the display unit 36.

Figure 5:
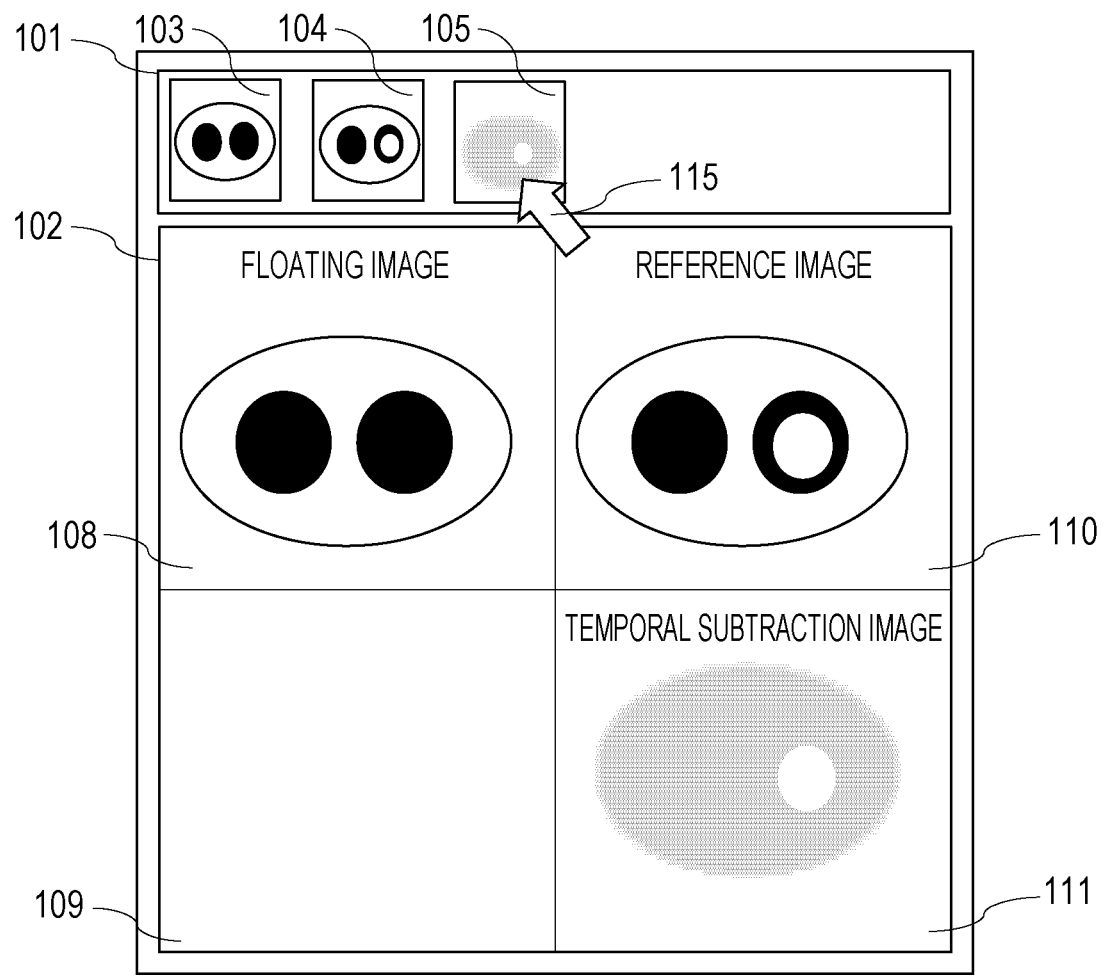
FIG. 5 illustrates a second example of a displayed screen in a process according to the first embodiment.

The processing in step S230 will be described more specifically. FIG. 5 illustrates an example display screen after the processing in S230 is executed. First of all, the display control unit 44 reads out the temporal subtraction image M105, the medical image M103, and the medical image M104 from the database 22. The medical image M103 being a floating image of the temporal subtraction image M105 is displayed in the region 108, the medical image M104 being a reference image of the temporal subtraction image M105 is displayed in the region 110, and the temporal subtraction image M105 is displayed in the region 111.

In step S240, the control unit 37 determines whether a user instructs to end the interpretation or not. The end of the interpretation may be instructed by clicking an end-of-interpretation button (not illustrated) on a mouse by the user. In response to the instruction to end the interpretation, the processing ends. Until the instruction to end the interpretation is input, the screen displayed on the display unit 36 may be maintained. Then, in response to a user's input for an operation for generating a thumbnail corresponding to a medical image not displayed in the medical image display region, the processing returns to step S210.

As described above, by selecting one thumbnail, a plurality of medical images corresponding to the thumbnail can be displayed in the medical image display region in a display form corresponding to the thumbnail. Thus, the user is not required to separately designate a display form of each of the plurality of medical images in a medical image display region, reducing user's time and effort associated with an interpretation work. The display unit 36 in the medical image display apparatus may include a plurality of monitors. In such a case, a wider medical image display region can be used, but inputting an operation for designating each of medical images may take user's time and effort. With the medical image display apparatus according to the first embodiment, an operation for selecting one thumbnail may be input to display a plurality of medical images on a medical image display region so that the time and effort for operation inputs can be reduced.

Next, a second embodiment of the present invention will be described. It is assumed that the components are implemented by software in a local environment. A case will be described in which a medical image display region is divided into a plurality of regions in advance before a user selects a thumbnail of a medical image to be displayed according to this embodiment. Hereinafter, a medical image display region before a thumbnail of a medical image is selected will be called a pre-selection display region. The division form for the pre-selection display region may be changed to a user's desirable form by using a known technology. Each of divided pre-selection display regions will be called a pre-selection division region.

Figure 9:
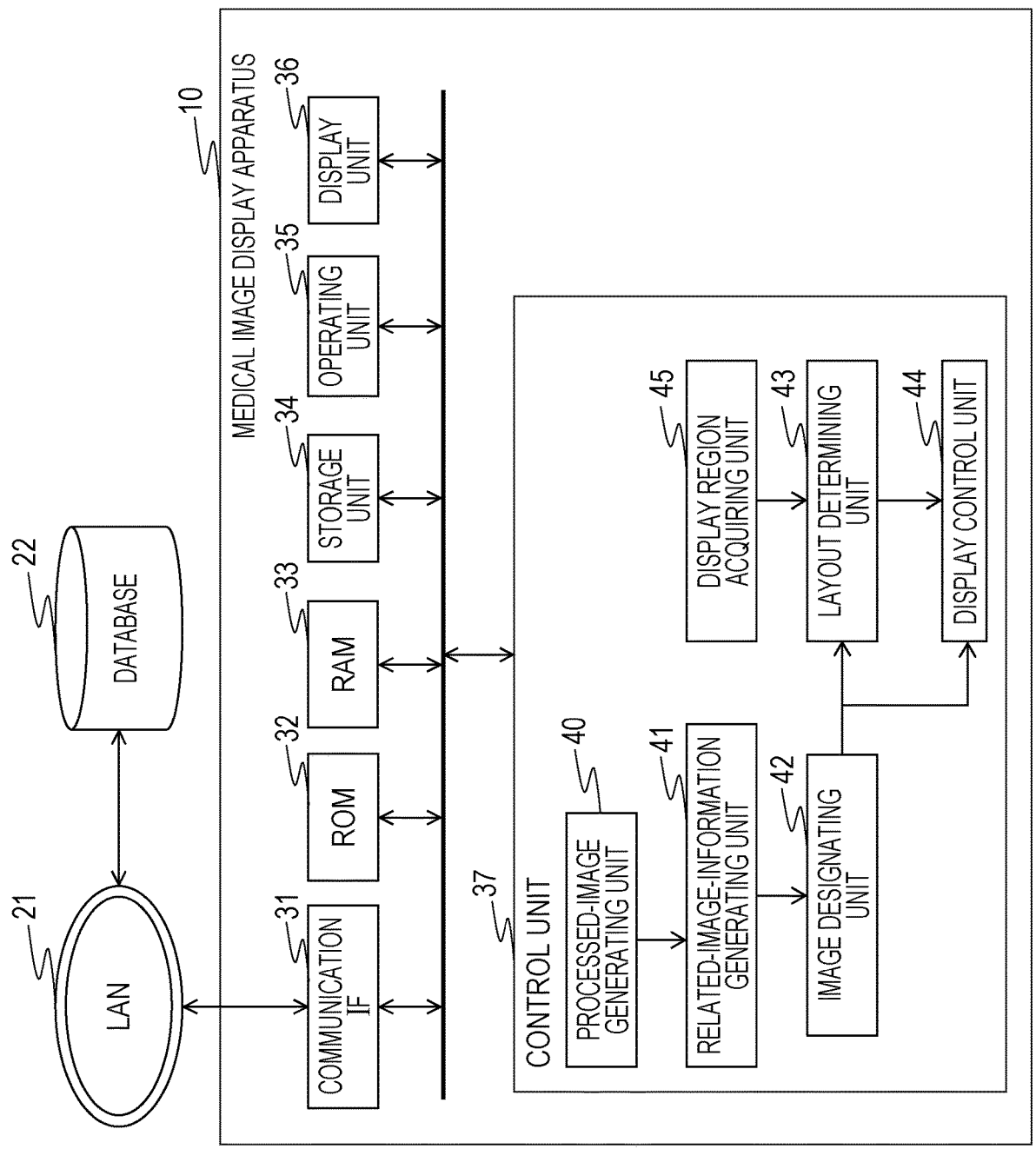
FIG. 9 is a block diagram illustrating a medical image display system according to a second embodiment.

FIG. 9 is a block diagram illustrating a medical image display system according to the second embodiment. The medical image display system according to the second embodiment of the present invention includes a display region acquiring unit 45 in addition to the medical image display system according to the first embodiment illustrated in FIG. 1 further. The functions of the components excluding the display region acquiring unit 45 are the same as the functions of the corresponding components illustrated in FIG. 1. The display region acquiring unit 45 acquires display region information of a region selected by a user and is output to the layout determining unit 43. The display region information is information describing a pre-selection division region selected by a user for displaying a medical image. In other words, the display region information is information describing a partial region related to an operation input for selection performed by a user among partial regions included in a medical image display region. The partial region may be one division region of a medical image display region or a combination of a plurality of division regions.

Figure 10A:
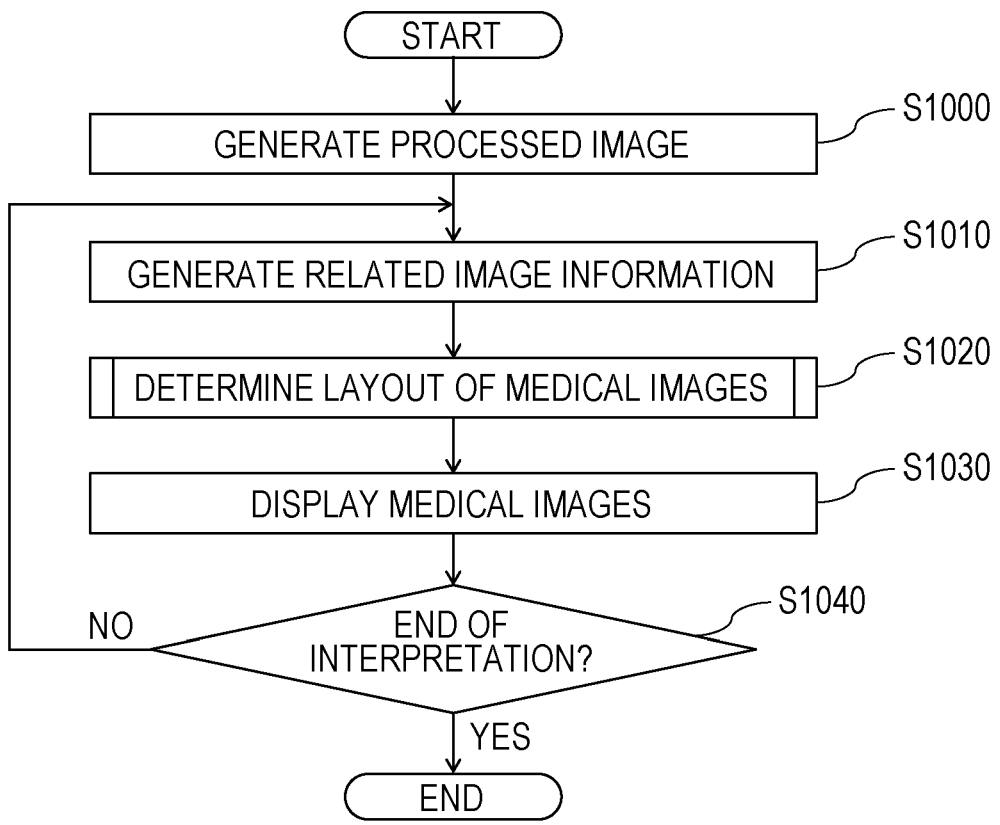
FIGS. 10A and 10B are flowcharts illustrating processes according to the second embodiment.
Figure 10B:
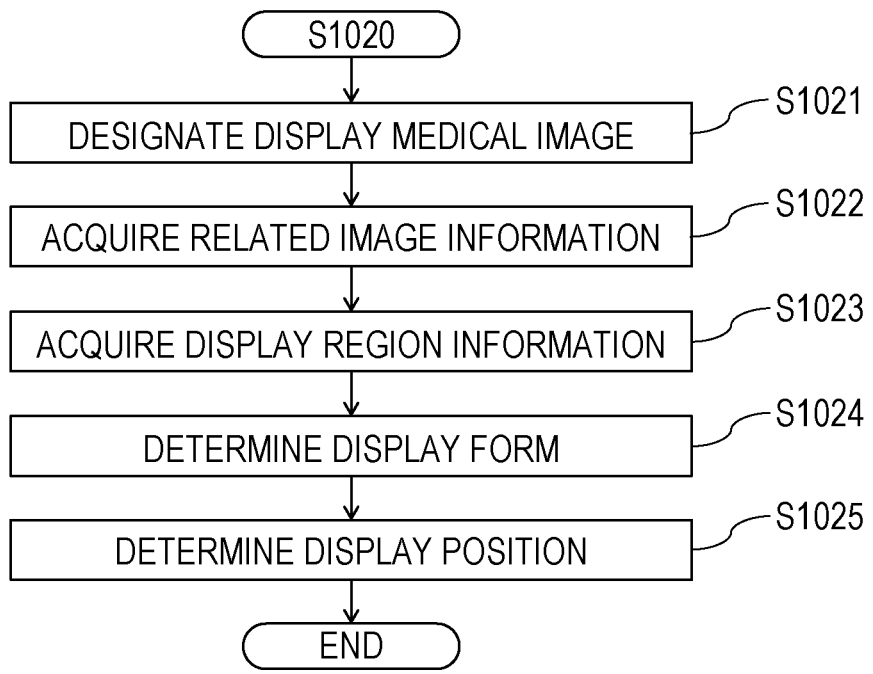

FIGS. 10A and 10B are flowcharts illustrating processing according to the second embodiment, and the control unit 37 executes the processing in each step. A case will be described in which a pre-selection display region is divided into four pre-selection division regions 108, 109, 110, and 111 in advance according to this embodiment, as illustrated in FIGS. 4A and 4B. It should be understood that the division form including the number of divisions and the sizes of the regions in a pre-selection display region according to this embodiment are given for illustration purpose, and embodiments of the present invention are applicable to any division forms.

The processing in step S1000 is the same as the processing in step S200 according to the first embodiment. It is assumed here that a deformable registration process and an image difference process are performed on the medical image M103 and the medical image M104 in step S1000, and the temporal subtraction image M105 is thus generated.

The processing in step S1010 is the same as the processing in step S210 according to the first embodiment. The thumbnail 103 of the medical image M103, the thumbnail 104 of the medical image M104, and the thumbnail 105 of the temporal subtraction image M105 are generated, and the thumbnails and medical images are associated under thumbnail rules. The related image information regarding each of the thumbnails is generated by acquiring the five information pieces. The thumbnails are displayed in a thumbnail display region, and the thumbnails and corresponding related image information are saved in the storage unit 34 in association with each other.

In step S1020, the layout determining unit 43 determines the position on the pre-selection division region selected by a user of a medical image associated with the thumbnail selected by the user. It should be noted that the processing in step S1020 is performed by following the flowchart in FIG. 10B.

In step S1021, a medical image corresponding to the thumbnail selected by a user is designated as a medical image to be displayed in the medical image display region.

In step S1022, for the thumbnail selected by the user, the related image information generated in step S1010 is acquired. In other words, the related image information corresponding to the medical image designated in step S1021 is acquired.

In step S1023, the display region acquiring unit 45 acquires information (which will be called display region information) regarding the display region selected by the user. It is assumed here that the pre-selection division region 110 is acquired as the display region information. It should be noted that a pre-selection division region is selected by a user by applying a known method. For example, the selection may be performed by dragging and dropping the thumbnail selected by the user in step S1020 to a target pre-selection division region. More specifically, a user may move a mouse pointer 115 onto the thumbnail 105, press a mouse button and move the mouse pointer 115 on the pre-selection division region 110 by keeping the mouse button pressed. Then, the button may be released with the mouse pointer 115 kept over the pre-selection division region 110 to execute the selection. In another example, a user may select a thumbnail to display a pre-selection division region at a position corresponding to the position over the thumbnail having undergone the input of the selection operation.

In step S1024, the display form of the pre-selection division region corresponding to the display region information acquired in step S1023 is set based on the related image information acquired in step S1022. Correspondences between related image information and display forms as illustrated in FIG. 7, for example, may be preset and the corresponding display form may be set based on the correspondence.

In step S1025, the display position of the medical image corresponding to the thumbnail is determined based on the display form set in step S1024 and the related image information acquired in step S1022. The display position determined here is a display position on the pre-selection division region corresponding to the display region information acquired in step S1023. Alternatively, correspondences among display forms, related image information, and display positions may be preset as illustrated in FIG. 8, for example, and the medical image may be displayed at the corresponding display position.

Figure 11:
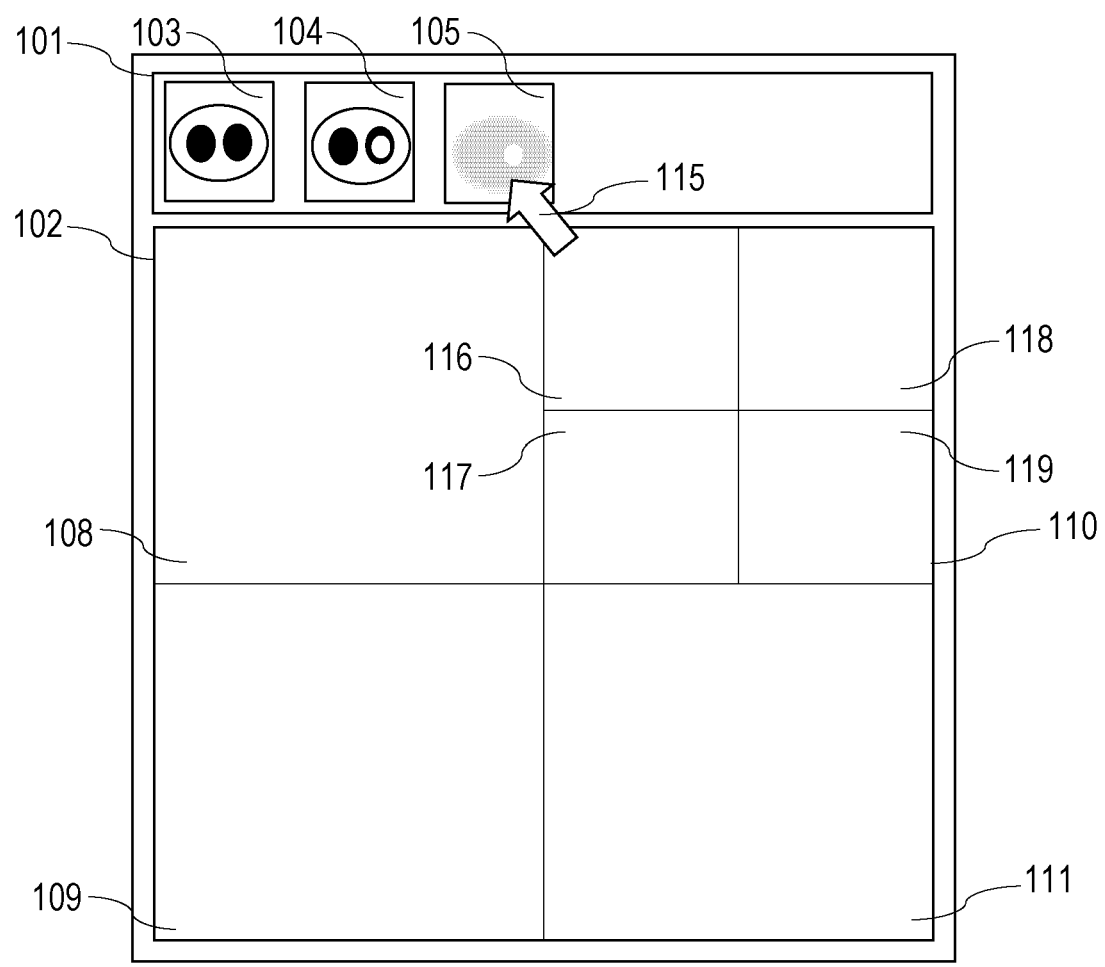
FIG. 11 illustrates an example in which one pre-selection division region is divided into a plurality of regions.

The processing in step S1020 will be described more specifically. A case will be described in which a user selects the thumbnail 105. FIG. 11 illustrates an example of one pre-selection division region divided into a plurality of regions and displayed on the display unit 36 after the processing in step S1020 completes. First, in step S1021, the image designating unit 42 in response to a user's operation input for selecting the thumbnail 105 designates the medical image M105 as a medical image to be displayed in the medical image display region. In step S1022, the layout determining unit 43 acquires related image information associated with the thumbnail 105. In other words, the number-of-thumbnail-associated image information is "3", and the type-of-thumbnail-associated image information is "temporal subtraction image". Referring to FIG. 7, the corresponding display form is R=2, C=2. In other words, the display region is divided such that the pre-selection division region 110 selected in step S1023 is to be displayed at the second row and the second column. More specifically, a display form is set in which the pre-selection division region 110 is divided into four regions 116, 117, 118, and 119. Next, the layout determining unit 43 acquires the related image information of the thumbnail 105 and information describing that the display form of the pre-selection division region 110 is R=2, C=2. Based on the correspondence relation illustrated in FIG. 8, it is determined to display an original image being a floating image at a position of Rn=1, Cn=1 on the pre-selection division region 110, that is, in the region 116. It is further determined to display an original image being a reference image at a position of Rn=1, Cn=2 on the pre-selection division region 110, that is, in the region 118. It is further determined to display a temporal subtraction image at a position of Rn=2, Cn=2 on the pre-selection division region 110, that is, in the region 119.

In a case where a user selects a medical image that is not a processed image, for example, when a user selects the thumbnail 104, the layout determining unit 43 acquires related image information associated with the thumbnail 104. In other words, "1" as the number-of-thumbnail-associated image information and "NULL" as the type-of-thumbnail-associated image information are acquired. In this case, because the number-of-thumbnail-associated image information is "1", it is determined not to divide the pre-selection division region 110 but arrange the medical image M104 in the pre-selection division region 110.

Figure 12:
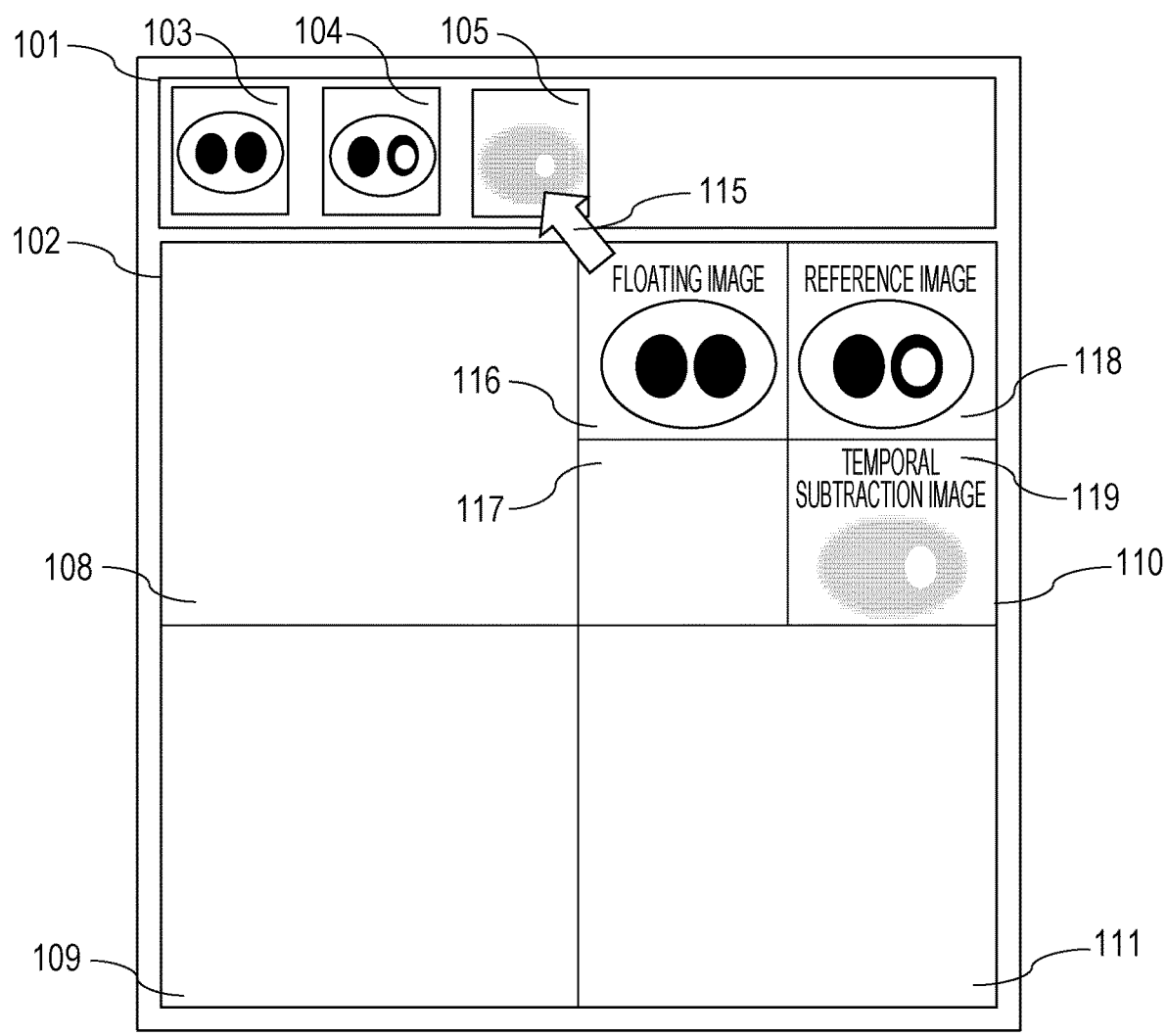
FIG. 12 illustrates a displayed screen example in a process according to the second embodiment.

In step S1030, the display control unit 44 reads out all medical images corresponding to the medical image designated in step S1020 from the database 22 or the storage unit 34 based on the thumbnail-associated image storage location information. All of the read medical images are arranged in the medical image display regions determined in the step S1020 and are displayed on the display unit 36. FIG. 12 illustrates a screen example displayed on the display unit 36 after the processing in step S1030 completes. First, the display control unit 44 reads out the temporal subtraction image M105, the medical image M103, and medical image M104 from the database 22. Then, the medical image M103 being a floating image of the temporal subtraction image M105 is displayed in the region 116 in the pre-selection division region 110, and the medical image M104 being a reference image of the temporal subtraction image M105 is displayed in the region 118. The temporal subtraction image M105 is then displayed in the region 119.

The processing in step S1040 is the same as the processing in step S240 in the first embodiment. If the end of the interpretation is instructed, the processing ends. Until the instruction to end the interpretation is input, the screen displayed on the display unit 36 is kept, and in response to a user's operation input for generation of a thumbnail of a medical image which is not displayed in the medical image display region, the processing returns to step S1010.

Figure 13:
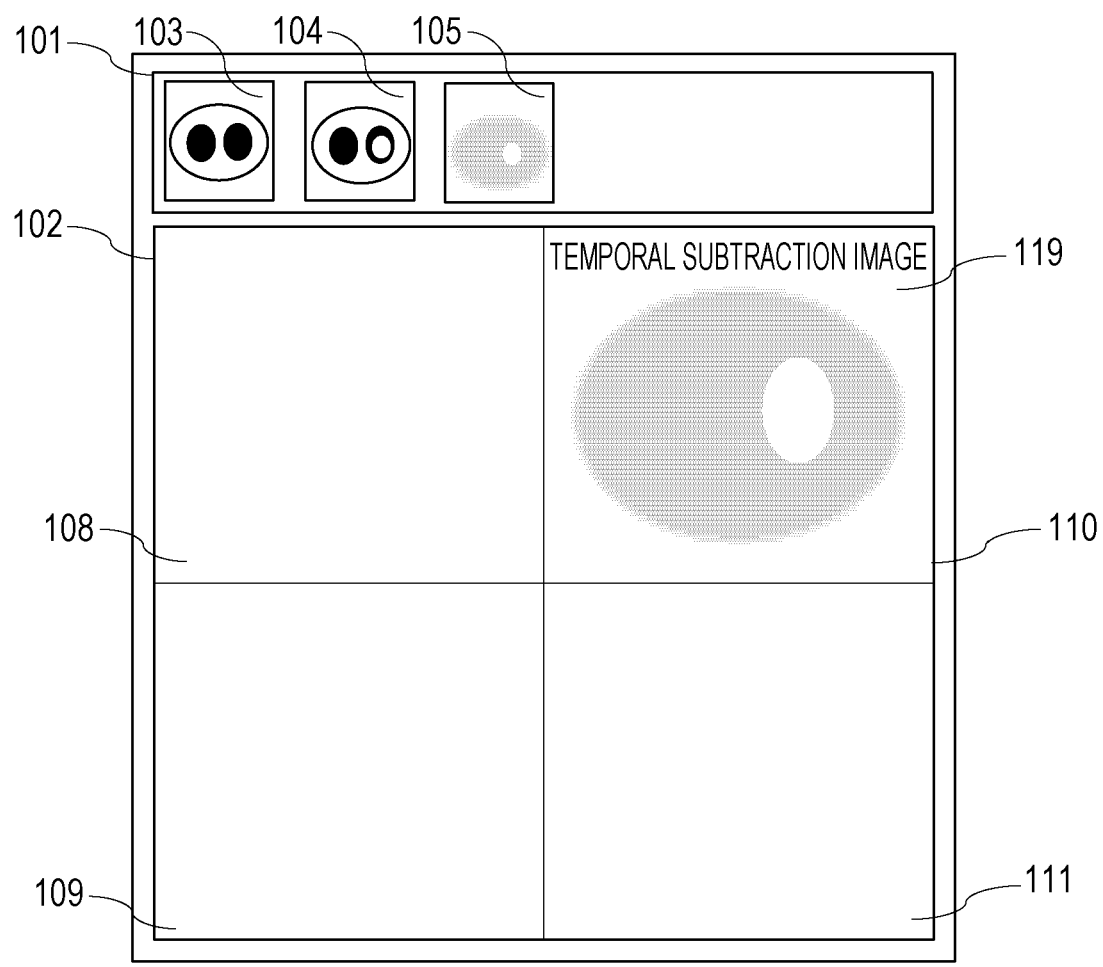
FIG. 13 illustrates a displayed screen example acquired by enlarging the size of one region of a pre-selection division region divided into a plurality of regions.

When a medical image display region is divided into a plurality of regions and a medical image is displayed in one of a plurality of division regions of one pre-selection division region as in the second embodiment, the following problems may possibly occur. A reduced size of regions for displaying medical images may prevent a user to easily observe the medical images. This problem may be solved by enlarging the sizes of regions to be displayed, for example. More specifically, a user may instruct to enlarge the size of the region 119 of the pre-selection division region 110 illustrated in FIG. 12 through the operating unit 35. The enlargement instruction may be input by a simple method to a user such as double-clicking or right clicking using a mouse being an example of the operating unit 35. Alternatively, the enlargement instruction may be input by a method in combination with a keyboard being an example of the operating unit 35. For example, clicking may be performed with a Shift button kept pressed. FIG. 13 illustrates a screen example to be displayed on the display unit 36 after a user inputs the enlargement instruction for the region 119. The medical image displayed in the region 119, that is, the temporal subtraction image M105 of this embodiment is then displayed in the pre-selection division region to which the region belongs, that is, over the whole pre-selection division region 110 of this embodiment. In response to such an operation, medical images displayed in a region excluding the region for which the enlargement is instructed, that is, on the regions 116, 117, and 118 of this embodiment are not displayed on the display unit 36. However, the layout in the pre-selection division region before a user instructs the enlargement is prestored in the storage unit 34. Thus, in response to input of an instruction to reduce the size of the enlarged region, the layout in the pre-selection division region can be returned to the state before the enlargement instruction is input. The instruction for reduction may be input by a simple method to a user such as right double-clicking using a mouse or clicking with a mouse wheel. Alternatively, the instruction may be input by a method in combination with a keyboard. For example, the clicking may be performed with a Ctrl button kept pressed. Different methods may be applied for inputting the enlargement instruction and the reduction instruction. For example, a left double-clicking operation may be performed on the region 119 as illustrated in FIG. 12 to enlarge the size of the temporal subtraction image M105 while a right double-clicking operation may be performed on the pre-selection division region 110 in FIG. 13 to return to the screen layout illustrated in FIG. 12. Thus, the size of a region having a small display size on the display unit 36 can easily be enlarged and can easily be returned to the state before the enlargement. Therefore, easy observation of the medical image can be achieved.

Figure 14:
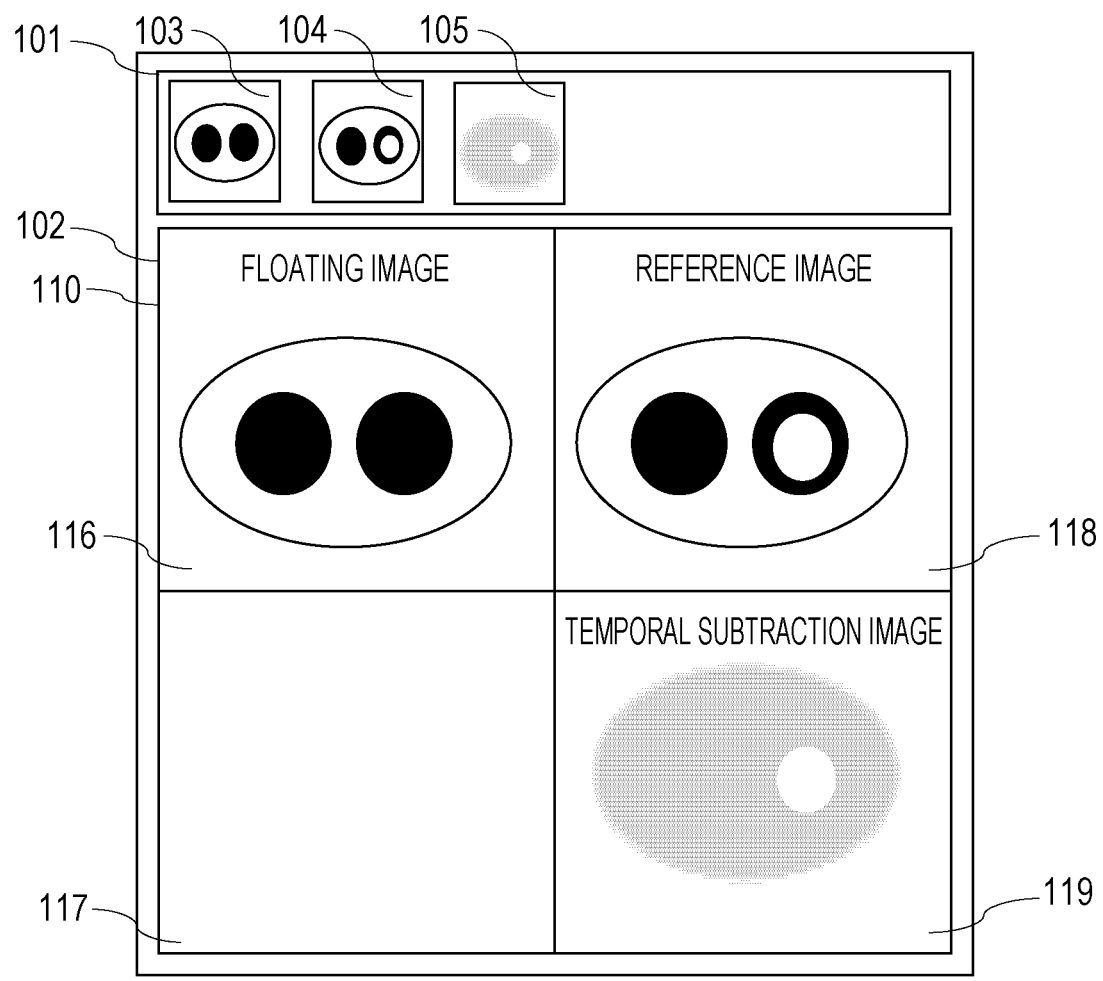
FIG. 14 illustrates a displayed screen example acquired by enlarging the size of a pre-selection division region divided into a plurality of regions.

In another example, the size of the entire pre-selection division region 110 is enlarged while maintaining the layout of the pre-selection division region 110. More specifically, a user may instruct to enlarge the size of the pre-selection division region 110 in FIG. 12 through the operating unit 35. The instruction for enlargement may be input by a simple method to a user such as left double-clicking or right clicking performed by using a mouse. Alternatively, the instruction may be input by a method in combination with a keyboard. For example, clicking may be performed with an Alt button kept pressed. These input methods may be different from the input method for enlarging or reducing the sizes of the regions within the pre-selection division region 110. According to this embodiment, when a left double-clicking of a mouse is performed by keeping pressing an Alt button on the keyboard on the pre-selection display region 110 in FIG. 12, the processing for enlarging the size of the whole pre-selection division region 110 is performed while maintaining the layout of the pre-selection division region 110. FIG. 14 illustrates a screen example displayed on the display unit 36 after the processing is executed. In other words, the whole medical image display region 102 is displayed while maintaining the layout of the whole pre-selection division region 110. The reduction operation for returning to the screen layout in FIG. 12 may be performed by right double-clicking of a mouse with an Alt button of a keyboard kept pressed, for example. The enlargement or reduction of the size of the entire pre-selection division region 110 and the enlargement or reduction of a region within the pre-selection division region may be instructed by a same input method but at different input positions. For example, referring to FIG. 12, when an enlargement is instructed in a region displaying a medical image (region 116, 118, or 119 here) of the pre-selection division region 110, the size of the medical image corresponding to the region is enlarged for display. When an enlargement is instructed in a region not displaying a medical image (region 117 here) of the pre-selection division region 110, the size of the whole pre-selection division region 110 is enlarged for display. In a case where an enlargement may be instructed by left clicking of a mouse, when a left double-clicking operation using the mouse is performed in the region 119, the medical image displayed in the region 119 is displayed in the entire pre-selection division region 110 as illustrated in FIG. 13. When a left double-clicking operation of the mouse is performed in the region 117, the entire pre-selection division region 110 is displayed in the entire medical image display region 102 as illustrated in FIG. 14. In another example, when an enlargement is instructed near a side edge of a pre-selection division region, the size of the pre-selection division region 110 may be enlarged.

Thus, the display form suitable for radiogram interpretation is maintained and at the same time the enlargement and reduction of the size of medical images can be easily performed as required for facilitating observation of the medical images.

In another example, medical images are displayed in a plurality of division regions of one pre-selection division region. Thus, the layout of the medical images can be maintained, and the size of a medical image for which an enlargement operation is instructed can be enlarged for display in a pre-selection division region where no other medical image is displayed. More specifically, a user may instruct to enlarge for the region 119 of the pre-selection division region 110 in FIG. 12 through the operating unit 35. At that time, no medical image is displayed in the region 108. Without changing the layout and details of medical images in the regions 116, 118, and 119, the temporal subtraction image M105 displayed in the region 119 is displayed in the entire region 108. Such enlargement instructions and reduction instructions may be input by different methods. This, all medical images to be compared may be kept displayed and at the same time the size of a medical image to be observed in more detail can be enlarged for facilitating the observation of the medical images.

As described above, in the medical image display apparatus according to the second embodiment of the present invention, one thumbnail and one pre-selection division region may be selected to display a plurality of medical images corresponding to the thumbnail in a display form corresponding to the thumbnail in an arbitrary pre-selection division region. This can save user's time and effort for performing radiogram interpretation work.

Next, a third embodiment of the present invention will be described. According to this embodiment, a case will be described in which a medical image is displayed in a pre-selection display region for displaying a medical image corresponding to a selected thumbnail.

Figure 15:
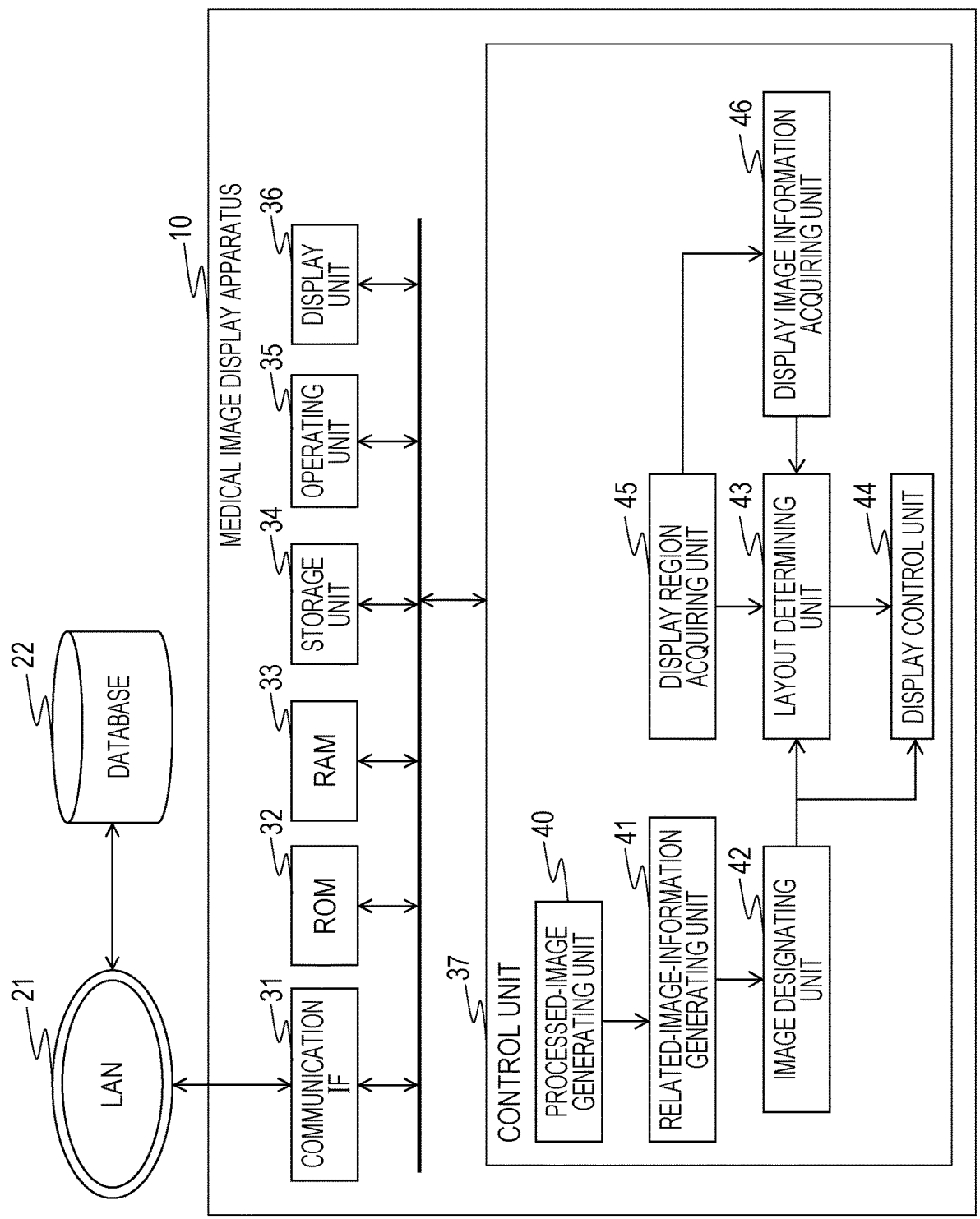
FIG. 15 is a block diagram illustrating a medical image display system according to a third embodiment.

FIG. 15 is a block diagram of a medical image display system according to a third embodiment of the present invention. The medical image display system according to the third embodiment includes an image information acquiring unit 46 in addition to medical image display system according to the second embodiment illustrated in FIG. 9. The functions of the components excluding the image information acquiring unit 46 are the same as the functions of the components illustrated in FIGS. 1 and 9. The image information acquiring unit 46 acquires information (hereinafter, called displayed image information) regarding a medical image displayed in a pre-selection division region corresponding to the display region information acquired by the display region acquiring unit 45 and outputs it to the layout determining unit 43. In other words, the image information acquiring unit 46 functions as a display acquiring unit configured to acquire such displayed image information. The displayed image information here includes the following two information pieces. A first information piece (hereinafter, called displayed image type information) is information describing the type of a medical image displayed in the pre-selection division region. In a case where a processed image is included in medical images displayed in the pre-selection division regions, the displayed image type information may be the processed-image type information regarding the processed image. In a case where no processed image is included in medical images displayed in the pre-selection division region, the displayed image type information is NULL. A second information piece (hereinafter, called displayed-image storage-location information) is information describing storage locations of all medical images displayed in pre-selection division regions corresponding to the display region information. These information pieces are saved in the storage unit 34 or the RAM 33 in association with pre-selection division regions when a medical image is displayed in the pre-selection division region. It should be understood that displayed image information pieces are given for illustration purpose and may be any information if the information can be acquired from the corresponding medical image, for example. It is assumed that the components are implemented by software in a local environment.

Figure 16A:
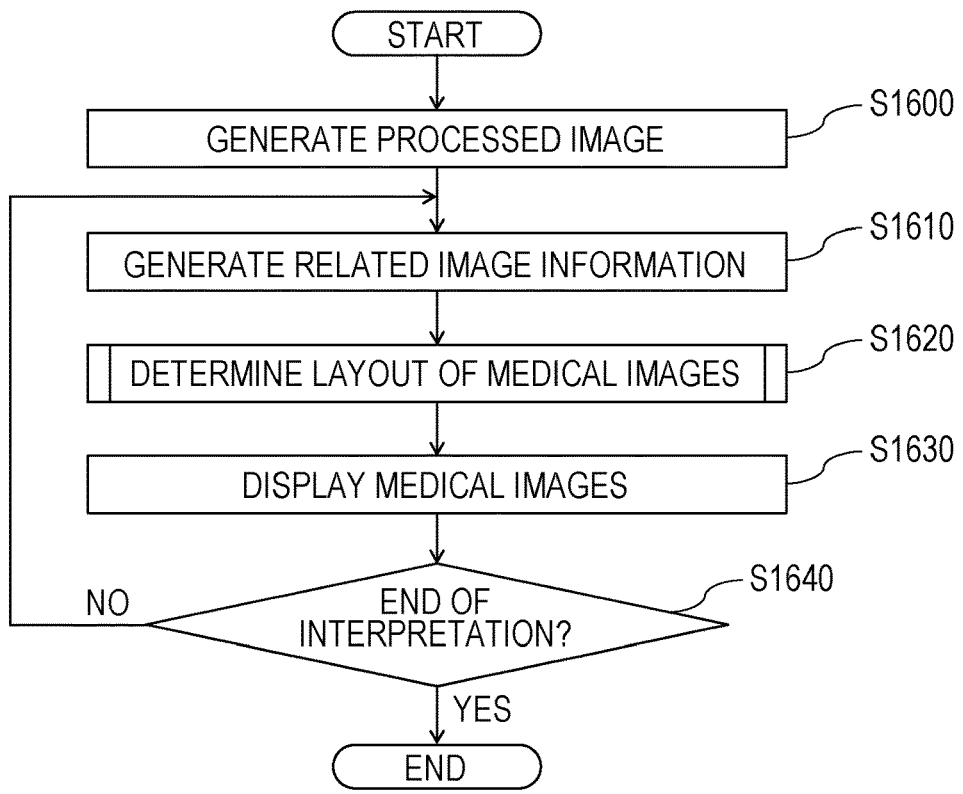
FIGS. 16A and 16B are flowcharts illustrating processes according to the third embodiment.
Figure 16B:
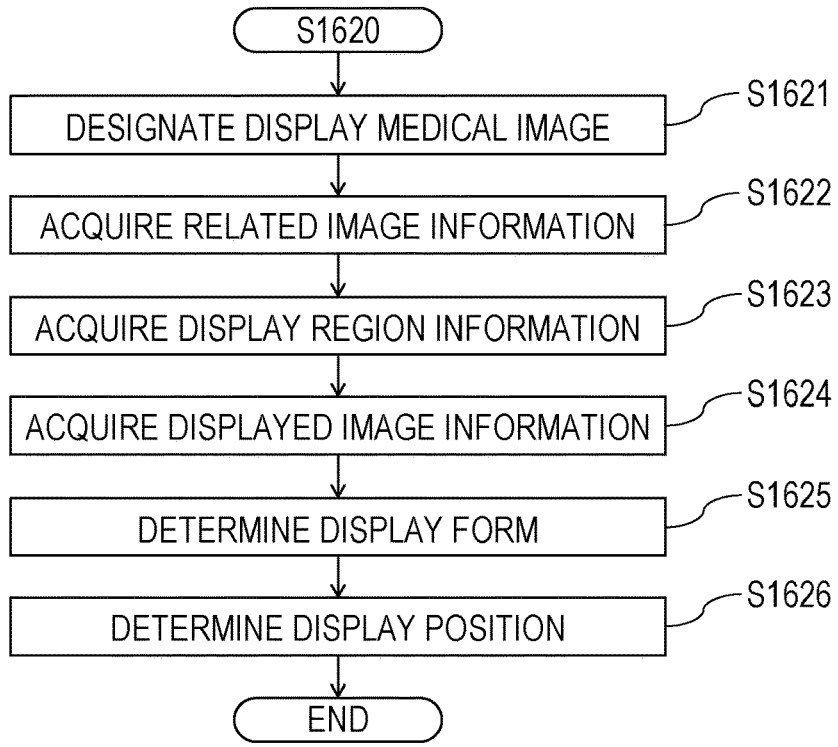

FIGS. 16A and 16B are flowcharts illustrating processing according to the third embodiment. The control unit 37 performs the processing in the flowcharts.

Figure 17:
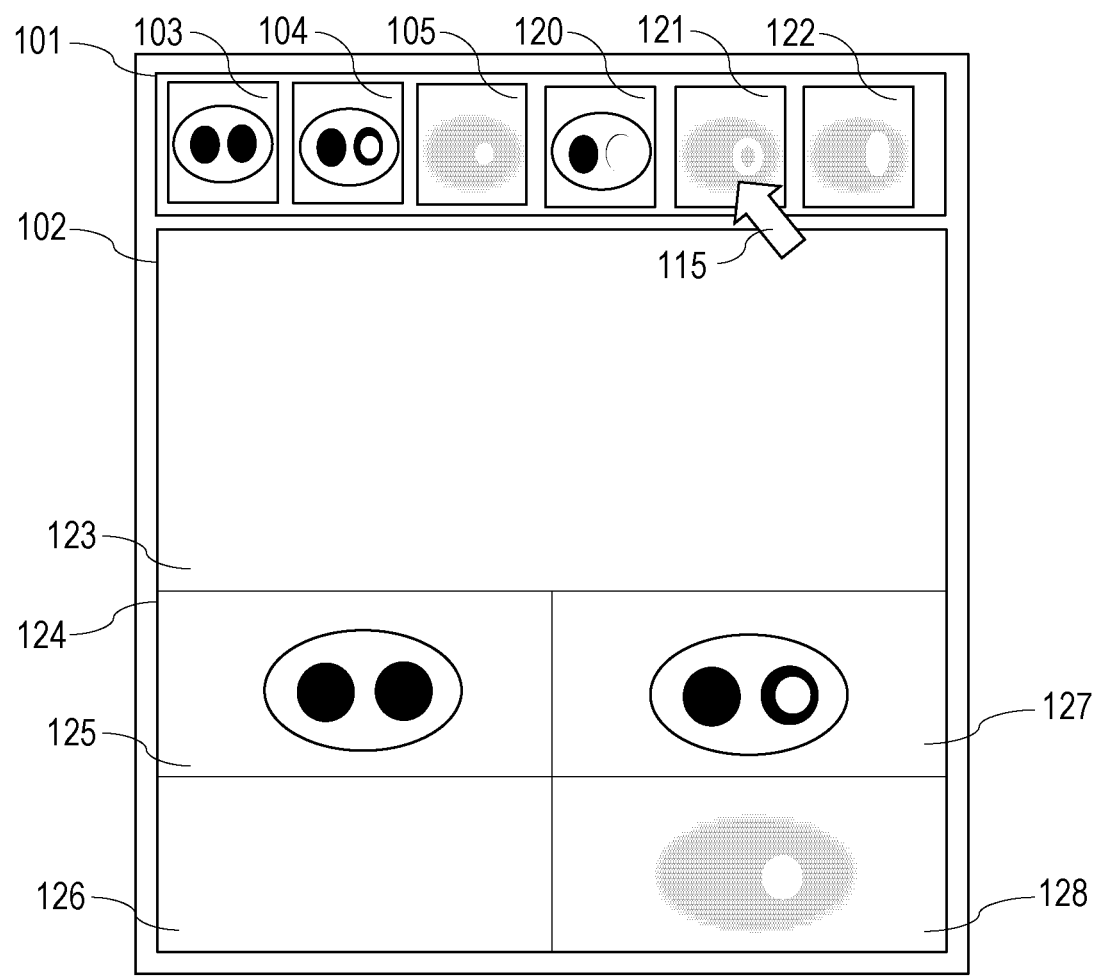
FIG. 17 illustrates a first example of a displayed screen in a process according to the third embodiment.

The processing in steps S1600 and S1610 is the same as the processing in steps S200 and S210 according to the first embodiment. FIG. 17 illustrates a screen example displayed on the display unit 36 after the processing up to step S1610 completes. Referring to FIG. 17, a thumbnail 103 is a thumbnail of a medical image M103 acquired by photographing one object by using a CT apparatus on Nov. 11, 2020. A thumbnail 104 is a thumbnail of a medical image M104 acquired by photographing the same object on Nov. 11, 2021. A thumbnail 120 is a thumbnail of a medical image M120 acquired by photographing the same object on Nov. 11, 2022. The same thumbnail rules as those of the first embodiment are applied in this embodiment. In other words, the thumbnail 103 is associated with the medical image M103, the thumbnail 104 is associated with the medical image M104, and the thumbnail 120 is associated with the medical image M120. A thumbnail 105 is a thumbnail of a temporal subtraction image M105 generated by performing known deformable registration and image difference processes on the medical image M103 and the medical image M104. Therefore, three medical images including the temporal subtraction image M105 being a processed image and the medical image M103 being a floating image and the medical image M104 being a reference image are associated with the thumbnail 105. A thumbnail 121 is a thumbnail of a temporal subtraction image M121 generated by performing known deformable registration and image difference processes on the medical image M120 and the medical image M104. Therefore, three medical images including the temporal subtraction image M121 being a processed image, the medical image M104 being a floating image and the medical image M120 being a reference image are associated with the thumbnail 121. A thumbnail 122 is a thumbnail of a temporal subtraction image M122 generated by performing known deformable registration and image difference processes on the medical image M120 and the medical image M103. Therefore, three medical images including the temporal subtraction image M122 being a processed image, the medical image M103 being a floating image and the medical image M120 being a reference image are associated with the thumbnail 122.

A case will be described in which a pre-selection display region is divided into two regions including a pre-selection division region 123 and a pre-selection division region 124 as illustrated in FIG. 17. FIG. 17 illustrates a state that nothing is being displayed in the pre-selection division region 123 and a medical image corresponding to the thumbnail 105 is being displayed in the pre-selection division region 124. The display in the pre-selection division region 124 is achieved by performing the processing according to the second embodiment. In other words, the medical image M103 is displayed in a region 125, the medical image M104 is displayed in a region 127, and the temporal subtraction image M105 is displayed in a region 128. The thumbnails and types of medical images associated thereto and the division form of the pre-selection display region according to this embodiment are given for illustration purpose, and the present invention is not limited thereto.

In step S1620, the layout determining unit 43 determines the position in the medical image display region of a medical image associated with a thumbnail selected by a user. It should be noted that the processing in step S1620 is performed by following the flowchart in FIG. 16B.

In step S1621, the medical image associated with the thumbnail selected by the user is designated as a medical image to be displayed in the medical image display region.

In step S1622, for the thumbnail selected by the user, the related image information generated in step S1010 is acquired. In other words, the related image information corresponding to the medical image designated in step S1021 is acquired.

In step S1623, the display region acquiring unit 45 acquires information (which will be called display region information) regarding a display region for displaying the medical image corresponding to the thumbnail selected by the user.

In step S1624, the image information acquiring unit 46 acquires displayed image information regarding medical images being displayed in the pre-selection division region corresponding to the display region information acquired in step S1623.

In step S1625, the display form of the pre-selection division region corresponding to the display region information acquired in step S1623 is changed based on the related image information acquired in step S1622 and the displayed image information acquired in step S1624. If the related image information and the displayed image information do not satisfy specific conditions, the display form of the pre-selection division region is set based on the related image information only, like the second embodiment. If the related image information and the displayed image information satisfy the specific conditions, the display form of the pre-selection division region is set based on both of the related image information and the displayed image information. The specific conditions are preset. The specific conditions are, for example, "the type-of-thumbnail-associated image information and the displayed image type information are identical" and "at least of medical images corresponding to the related image information and at least one of medical images corresponding to the displayed image information are identical". The specific conditions may be changed as required while a user is using the medical image display system. It is assumed that the display form in a case where the related image information and the displayed image information satisfy the specific conditions are preset. FIG. 19 illustrates a correspondence example between the processed-image type information and display forms under the specific conditions.

In step S1626, the layout determining unit 43 determines the display position based on the display form set in step S1625, the related image information acquired in step S1622, and the displayed image information acquired in step S1624. The display position to be determined here is a display position in the pre-selection division region corresponding to the display region information acquired in step S1623. If the related image information and the displayed image information do not satisfy the specific condition in step S1625, the display position is determined based on the correspondence relation preset like the second embodiment. If they satisfy the specific conditions, the display position is determined based on the preset correspondences between type-of-thumbnail-associated image information and display positions, as illustrated in FIG. 20, for example. FIG. 20 illustrates a correspondence example between processed-image type information and display positions under the specific conditions. It is assumed that the correspondence relation is preset. For example, in a case where the processed image is a temporal subtraction image, a reference image and the temporal subtraction image corresponding to the reference image at an identical position on an image of an anatomical structure are aligned vertically on a display screen. For that, a correspondence relation satisfying a condition "a reference image and all temporal subtraction images corresponding to the reference image are arranged on an identical column or row" may be preset. For easy observation by a user, when a plurality of temporal subtraction images is generated, the temporal subtraction images corresponding to an identical floating image are displayed horizontally. Therefore, a correspondence relation satisfying a condition "all temporal subtraction images corresponding to an identical floating image are arranged on an identical column or row" may be preset. From another point of view, for easy observation by a user of temporal subtraction images to be compared, temporal subtraction images corresponding to different floating images are not displayed on one column or row in a case where a plurality of temporal subtraction images is generated. Therefore, a correspondence relation satisfying a condition "temporal subtraction images corresponding to different floating images are arranged on different columns or rows" may be preset. As another example, in a case where the processed images are MIP images or MIniP images, the MIP images or MIniP images corresponding to an identical original image are displayed horizontally. Therefore, a correspondence relation satisfying a condition "all MIP images or MIniP images corresponding to an identical original image are arranged on an identical column or row" may be preset. As another example, in a case where the processed images are superimposed images, a layer image and a superimposed image corresponding to the layer image are displayed vertically for easy observation by a user. Therefore, a correspondence relation satisfying a condition "a layer image and all superimposed images corresponding to the layer image are arranged on an identical column or row" may be preset. For easy observation by a user, in a case where a plurality of superimposed images is generated, superimposed images corresponding to an identical base image are displayed horizontally. Therefore, a correspondence relation satisfying a condition "all superimposed images corresponding to an identical base image are arranged on an identical column or row" may be preset. For easy observation by a user, in a case where a plurality of superimposed images are generated, superimposed images corresponding to different base images are not displayed on one column or row. Therefore, a correspondence relation satisfying a condition "all superimposed images corresponding to different base images are arranged on different columns or rows" may be preset. It should be understood that the correspondence relation between type-of-thumbnail-associated image information and display positions is given for illustration purpose, and the present invention is not limited thereto. The correspondence relation may be changed as required while a user is using the medical image display system.

Figure 18:
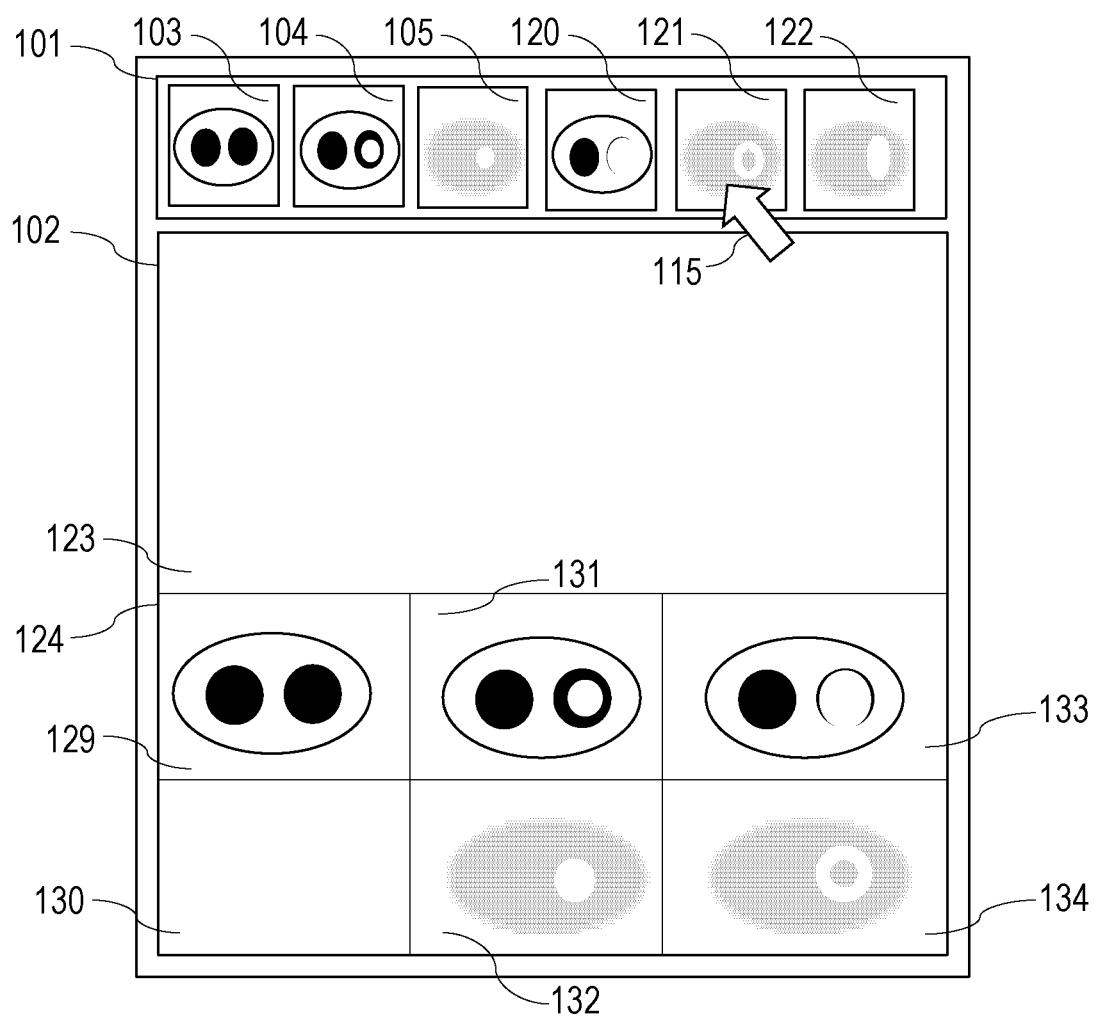
FIG. 18 illustrates a second example of a displayed screen in a process according to the third embodiment.

The processing in step S1620 will be described more specifically. The following description assumes that a user selects the thumbnail 121. First, in step S1621, the image designating unit 42 in response to a user's operation input for selecting the thumbnail 121 designates the medical image M121 as a medical image to be displayed on the medical image display region. In step S1622, the following information is acquired as the related image information regarding the thumbnail 121. The number-of-thumbnail-associated image information is "3", and the type-of-thumbnail-associated image information is "temporal subtraction image". Further as thumbnail-associated image storage location information, storage destination paths in the storage unit 34 of the temporal subtraction image M121, the medical image M104, and the medical image M120 are acquired. In step S1623, it is determined that a user selects the pre-selection division region 124 as a display region, and the display region acquiring unit 45 acquires the pre-selection division region 124 as display region information. In the pre-selection division region 124 in the example illustrated in FIG. 17, the region 125 displays the medical image M103, the region 127 displays the medical image M104, and the region 128 displays the temporal subtraction image M105. In step S1624, a "temporal subtraction image" is acquired as displayed image type information because the temporal subtraction image M105 is a processed image. As displayed-image storage-location information, the storage destination paths of the temporal subtraction image M105, the medical image M103, and the medical image M104 are acquired. The specific conditions here are assumed as "type-of-thumbnail-associated image information and displayed image type information are identical" and "at least one of medical images corresponding to the related image information and at least one of medical images corresponding to the displayed image information are identical". According to this embodiment, both of the type-of-thumbnail-associated image information and the displayed image type information are "temporal subtraction images" and are identical. The medical image M104 being a floating image of the temporal subtraction image M121 corresponding to the related image information and the medical image M104 being a reference image of the temporal subtraction image M105 corresponding to the displayed image information are identical. Therefore, this embodiment satisfies the specific conditions. Next, referring to FIG. 19, because the type-of-thumbnail-associated image information is "temporal subtraction images", the number of rows (R) is equal to "the highest number of numbers of temporal subtraction images corresponding to the reference images+1". The number of columns (C) is equal to "the total number of different original images". First, R will be described. According to this embodiment, all of medical images corresponding to a thumbnail selected by a user and medical images displayed in a pre-selection division region selected by the user correspond to the following two reference images. That is, the reference images are the medical image M120 being a reference image of the temporal subtraction image M121 and the medical image M104 being a reference image of the temporal subtraction image M105. In addition, the medical image M120 corresponds to only one temporal subtraction image M121, and the medical image M104 corresponds to only one temporal subtraction image M105. Therefore, R=2 because "the highest number of numbers of temporal subtraction images corresponding to the reference images" is equal to "1". Next, C will be described. According to this embodiment, all of medical images corresponding to a thumbnail selected by a user and a medical image displayed in a pre-selection division region selected by the user correspond to the following three original images. That is, the original images include the medical image M104 being a floating image and the medical image M120 being a reference image of the temporal subtraction image M121, and the medical image M103 being a floating image and the medical image M104 being a reference image of the temporal subtraction image M105. In other words, because three different original images including the medical image M104, the medical image M120, and the medical image M103 correspond thereto, C=3. FIG. 18 illustrates a screen example displayed on the display unit 36 after the processing up to step S1630 completes. For example, as illustrated in FIG. 18, the pre-selection division region 124 is divided into six regions of regions 129, 130, 131, 132, 133, and 134. In step S1626, with reference to FIG. 20, a display position corresponding to "temporal subtraction image" as the type-of-thumbnail-associated image information is determined. First, under condition a., the original image is arranged in region of Rn=1. Describing with reference to FIG. 18, it is determined to arrange the medical images M120, M104, and M103 in the regions 129, 131, and 133, respectively. Next, under condition b., the photographed date of the original image is checked. The medical image M103, the medical image M104, and the medical image M120 are photographed at dates in that order according to this embodiment. Therefore, it is determined to display the medical image M103 in the region 129, and the medical image M104 in the region 131, and the medical image M120 in the region 133. Next, under condition c. relating to the display positions, it is determined to display a temporal subtraction image in a region of Rn=2. Referring to FIG. 18, it is determined to arrange the temporal subtraction images 105 and M121 in the regions 130, 132, and 134. Next, under condition d. relating to display positions, because the reference image of the temporal subtraction image M105 is the medical image M104, it is determined to arrange the temporal subtraction image M105 and the medical image M104 on a column having an identical column number, that is, a column of Cn=2. Because the reference image of the temporal subtraction image M121 is the medical image M120, it is determined to arrange the temporal subtraction image M121 and the medical image M120 on an column having an identical column number, that is, a column of Cn=3. Finally, under condition e., the row number for displaying the temporal subtraction images is determined. According to this embodiment, because a plurality of temporal subtraction images is not arranged on a column having an identical column number, it is determined to display the temporal subtraction image M105 in the region 132 and the temporal subtraction image M121 in the region 134. It should be understood that those display positions are given for illustration purpose and the present invention is not limited thereto.

In step S1630, medical images corresponding to the related image information acquired in step S1622 are read out from the database 22 or the storage unit 34 through the communication IF 31 and the LAN 21 based on the thumbnail-associated image storage location information. The medical images corresponding to the displayed image information acquired in step S1624 are read out from the database 22 or the storage unit 34 through the communication IF 31 and the LAN 21 based on the displayed-image storage-location information. All of the read out medical images are arranged in the medical image display region determined in step S1620 and are displayed on the display unit 36.

The processing in step S1630 will be described more specifically. First, the display control unit 44 reads out the temporal subtraction image M121, the medical image M104 being a floating image and the medical image M120 being a reference image from the database 22. The temporal subtraction image M105, the medical image M103 being a floating image, and the medical image M104 being a reference image are further read out. Here, because the medical image M104 is common, it may be readout once. The display control unit 44 then displays the medical image M103 in the region 129, the medical image M104 in the region 131, and the medical image M120 in the region 133 in the pre-selection division region 124. The display control unit 44 further displays the temporal subtraction image M105 in the region 132 and the temporal subtraction image M121 in the region 134.

The processing in step S1640 is the same as the processing in step S240 according to the first embodiment. If end of the radiogram interpretation is instructed, the processing ends. Until the instruction to end interpretation is input, the screen displayed on the display unit 36 may be maintained. Then, in response to a user's input for an operation for generating a thumbnail corresponding to a medical image not displayed in the medical image display region, the processing returns to step S1610.

Figure 21:
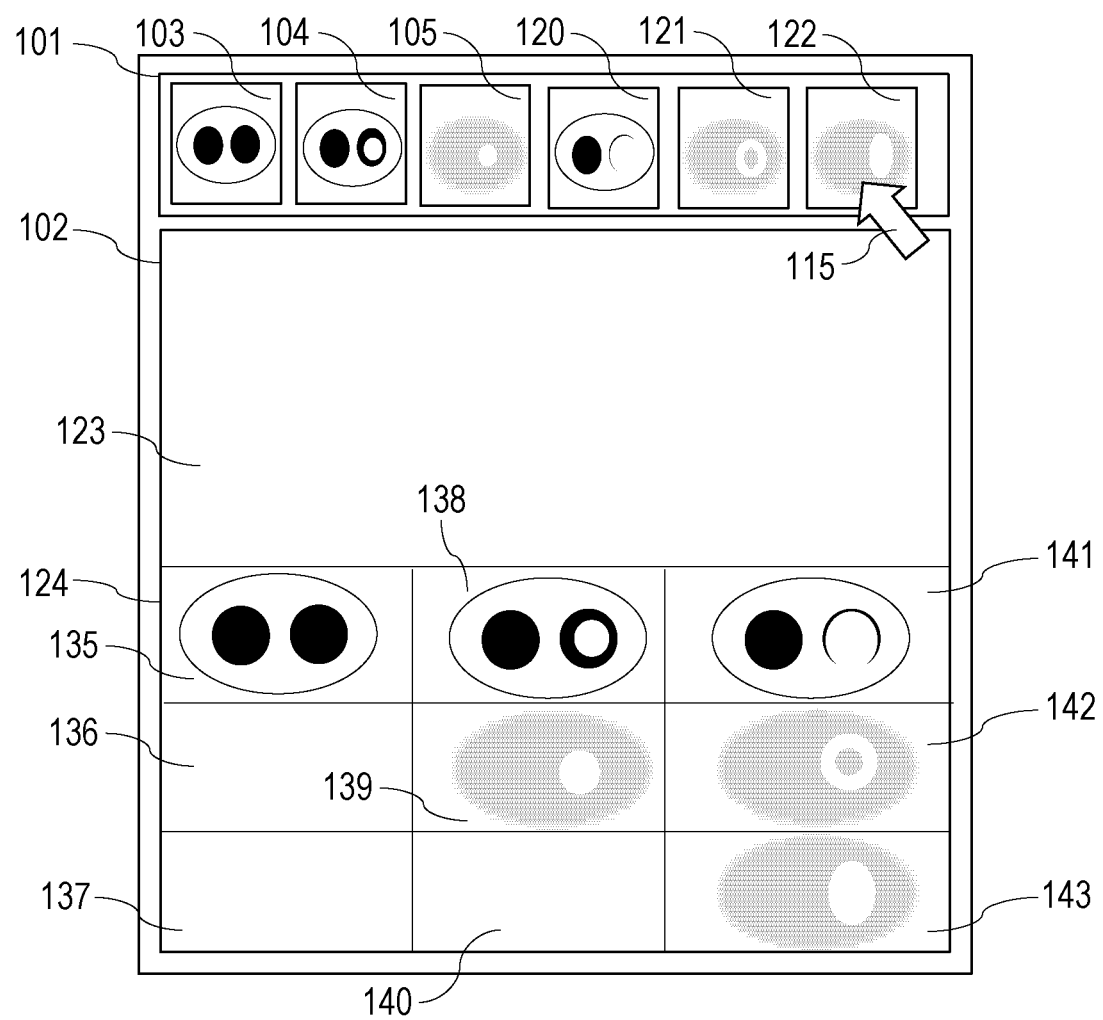
FIG. 21 illustrates a third example of a displayed screen in a process according to the third embodiment.

In the example above, when the processing up to step S1630 completes, the display unit 36 displays the screen illustrated in FIG. 18. A case will be described in which the processing returns to step S1610 in response to a user's operation input for selecting a thumbnail of a medical image. For example, it is assumed that a user selects the thumbnail 122 and selects the pre-selection division region 124 as the display region for a medical image corresponding to the thumbnail. In this case, in step S1622, "3" as number-of-thumbnail-associated image information and "temporal subtraction image" as type-of-thumbnail-associated image information are acquired. Furthermore, as thumbnail-associated image storage location information, the storage destination paths in the storage unit 34 of the temporal subtraction image M122, the medical image M103 being a floating image, and the medical image M120 being a reference image are acquired. Next, in step S1623, the pre-selection division region 124 is acquired as display region information. Next, in step S1624, "temporal subtraction image" is acquired as displayed image type information. Furthermore, as displayed-image storage-location information, the storage destination paths in the storage unit 34 of the temporal subtraction image M105, the temporal subtraction image M121, the medical image M103, the medical image M104, and the medical image M120 are acquired. Next, in step S1625, the pre-selection division region 124 is divided to have R=3, C=3 with reference to FIG. 19. In other words, as illustrated in FIG. 21, the pre-selection division region 124 is divided into nine regions of regions 135 to 143. Next, in step S1626, the display positions in the pre-selection division region 124 of the medical images are determined with reference to FIG. 20. Next, in step S1630, the medical images are displayed based on the positions determined in step S1620. That is, the medical image M103 is displayed in the region 135, the medical image M104 in the region 138, and the medical image M120 in the region 141. The temporal subtraction image M105 is displayed in the region 139, the temporal subtraction image M121 in the region 142, and the temporal subtraction image M122 in the region 143.

As described above, in the medical image display apparatus according to the third embodiment, one thumbnail and one pre-selection division region may be selected to display a plurality of medical images corresponding to the thumbnail and the pre-selection division region in one pre-selection division region. Therefore, a user can easily display all of a plurality of highly related medical images in one region and can perform radiogram interpretation work with less time and effort.

From a display point of view, the aforementioned embodiments may provide the following functions. The layout determining unit 43 determines a position of a medical image to be displayed in a medical image display region by performing the processing as described above before a user confirms an operation input for selecting the medical image. More specifically, assuming that a mouse is used as the operating unit 35 for operation input, when a mouse pointer is displayed over a thumbnail, the image designating unit 42 assumes that the thumbnail has is selected and controls the layout determining unit 43 to determine a layout in the medical image display region. A screen with the determined layout is displayed on the display unit 36 through the display control unit 44. Because the user has not confirmed the operation input for selecting the medical image yet, the medical image may be displayed in a different way from a medical image after the operation input for the selection is confirmed. For example, the display control unit 44 may control such that a medical image before the operation input for selection is confirmed may be displayed in light color. In another example, the medical image display region or the pre-selection display region may be displayed with a broken line indicating a division form based on the number of rows and the number of columns acquired by the layout determining unit 43. A user may preset a correspondence relation as illustrated in FIG. 7 or 8. When a plurality of layouts based on the set correspondence relation exists, the layout to be used for display may be selected from the plurality of layouts, and the layout of medical images to be displayed may be confirmed in response to the user's selection.

In other words, the control unit 37 in the information processing apparatus and information processing system according to any of the aforementioned embodiments is configured to select a medical image to be displayed in a medical image display region. The control unit 37 selects a medical image to be displayed in response to the confirmation of the operation input for the selection. Alternatively, the control unit 37 determines and selects a medical image possibly to be selected based on an input from the operating unit 35 even when the operation input for selection has not been confirmed.

The information processing apparatus and information processing system according to any one of the aforementioned embodiments may be implemented as a single apparatus, or apparatus including a plurality of information processing devices may be communicably coupled to each other to execute the processing as described above, either of which may be included in embodiments of the present invention. A common server apparatus or server group may execute the processing as described above. In this case, the common server apparatus corresponds to an information processing apparatus according to an embodiment, and the server group corresponds to an information processing system according to an embodiment. A plurality of apparatuses included in the information system or information processing system may only be required to be capable of communication at a predetermined communication rate and may not be required to be present within one facility or one country.

In a case where the information processing apparatus and information processing system according to any one of the aforementioned embodiments are implemented as a server apparatus or a server group, the display control unit 44 may function as a display output unit configured to output in a manner that the layout determined by a layout determining unit is displayable.

Embodiments of the present invention may include an embodiment in which a software program implementing functionality of any one of the aforementioned embodiments may be supplied to a system or an apparatus, and a computer in the system or the apparatus may read out and execute code of the supplied program.

Therefore, the program code installed in a computer for causing the computer to execute the processing according to an embodiment is also an embodiment of the present invention. Based on an instruction included in a program read out by such a computer, an OS running on the computer may execute a part or all of actual processing so that the processing can implement the functionality of any one of the aforementioned embodiments.

Combinations of the aforementioned embodiments may also be included in embodiments of the present invention.

According to the present invention, the display form for displaying a plurality of related medical images in a display region can be determined without requiring an operation to be performed on each of the medical images.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-118357, filed Jun. 11, 2015, and No. 2015-157652, filed Aug. 7, 2015 which are hereby incorporated by reference herein in their entirety.

What is claimed is:

1. An information processing apparatus comprising:
 a first acquiring unit configured to acquire a processed image, wherein the acquired processed image was newly created by processing at least one medical image;
 an accepting unit configured to accept a display instruction based on an operation input by a user;
 a storage unit configured to store related image information including information regarding a type of the processing and the at least one medical image used for the processing;
 a second acquiring unit configured to acquire the related image information; and
 a display control unit configured to display, as instructed by the display instruction, at least one image in a medical image display region including a plurality of partial regions,
 wherein, in a case where the accepted display instruction is a direct display instruction for the processed image and the accepted display instruction is not a direct display instruction for the at least one medical image used for the processing, the display control unit displays, in the plurality of partial regions, the processed image and the at least one medical image used for the processing, based on the related image information acquired by the second acquiring unit, and
 wherein the display control unit further divides the medical image display region into the plurality of partial regions based on information regarding the processing type, and to display the processed image and the at least one medical image used for the processing in accordance with a layout determined based on the related image information in the plurality of partial regions.

2. The information processing apparatus according to claim 1,
 wherein the display control unit is configured to display a thumbnail of a medical image in a thumbnail display region, and
 wherein the accepting unit is configured to accept a display instruction for a processed image corresponding to a corresponding thumbnail in response to a thumbnail operation input performed on the medical image thumbnail displayed in the thumbnail display region.

3. The information processing apparatus according to claim 2, wherein the display control unit is configured to display the processed image in a region specified based on the thumbnail operation input performed on the corresponding thumbnail.

4. The information processing apparatus according to claim 2, further comprising an associating unit configured to associate the related image information including information regarding the processing type and information regarding the at least one medical image used for the processing.

5. The information processing apparatus according to claim 1, wherein the display control unit is configured to divide a partial region identified in accordance with a thumbnail operation input on a thumbnail, and to display the processed image and a medical image used for the processing in divided partial regions.

6. The information processing apparatus according to claim 1, further comprising a display acquiring unit,
 wherein, in a case where a medical image is displayed in a partial region identified in accordance with a thumbnail operation input on a thumbnail, the display acquiring unit i acquires displayed image information, wherein the acquired displayed image information is information regarding the displayed medical image, and wherein the display control unit is configured to display the processed image and a medical image used for the processing in the medical image display region based on the acquired displayed image information and the related image information.

7. The information processing apparatus according to claim 1, wherein each of the plurality of partial regions is capable of displaying one medical image, and wherein the display control unit is configured to display the processed image on a column or row that, respectively, is different from a column or row of the at least one medical image used for the processing among the plurality of partial regions identified based on a column number and a row number.

8. The information processing apparatus according to claim 7, wherein, in a case where the processed image is a maximum intensity projection image, the display control unit displays, on an identical column or an identical row, a plurality of processed images generated by using maximum intensity projection on an identical image.

9. The information processing apparatus according to claim 7, wherein, in a case where the processed image is a minimum intensity projection image, the display control unit displays, on an identical column or an identical row, a plurality of processed images generated by using minimum intensity projection on an identical image.

10. The information processing apparatus according to claim 7, wherein, in a case where the processed image is an acquired superimposed image acquired by superimposing a plurality of different medical images, the display control unit displays, on an identical column or an identical row, all superimposed images corresponding to a layer image among a base image, wherein the base image is a base medical image of the superimposing of the plurality of different medical images, wherein the layer image is a medical image to be superimposed on the base image, and wherein a superimposed image is a processed image corresponding to the layer image.

11. The information processing apparatus according to claim 10, wherein the display control unit displays, on an identical column or an identical row, a plurality of superimposed image corresponding to an identical base image, and wherein the display control unit displays a plurality of superimposed images not corresponding to an identical base image on different columns or different rows.

12. The information processing apparatus according to claim 1, wherein the processed image is one of a temporal subtraction image acquired by subtracting a plurality of medical images of an identical object acquired at different time points, a maximum intensity projection image acquired by displaying a highest value in a projection path in an arbitrary view direction of a three-dimensional image onto a plane of projection, a minimum intensity projection image acquired by displaying a lowest value in a projection path in an arbitrary view direction of a three-dimensional image on to a plane of projection, or a superimposed image acquired by superimposing a plurality of different medical images for display.

13. The information processing apparatus according to claim 12, wherein the plurality of medical images of the identical object acquired at different time points includes a first medical image and a second medical image acquired at a point in time before the first medical image, and wherein, in a case where the processed image is a temporal subtraction image acquired by subtracting the second medical image from the first medical image, the display control unit displays, on an identical column or an identical row, the first medical image and a processed image acquired by temporal subtraction.

14. The information processing apparatus according to claim 1, wherein, in a case where the accepted display instruction is not a display instruction for the processed image, the display control unit displays a medical image instructed by the accepted display instruction in a partial region in the medical image display region.

15. The information processing apparatus according to claim 1, wherein the storage unit is configured to store, in association with each other, the processed image, the at least one medical image used for the processing, and the related image information.

16. The information processing apparatus according to claim 1, wherein processing the at least one medical image is by subtraction.

17. The information processing apparatus according to claim 1, wherein the acquired processed image is a subtraction image.

18. An information processing apparatus comprising:

a storage unit configured to store, as storage information, a processed image and related image information including at least one of (i) information regarding at least one medical image used for processing and a type of the processing, (ii) information regarding the processing type, and (iii) information regarding the at least one medical image used for the processing in association with each other, wherein the stored processed image was newly created by processing the at least one medical image;

an accepting unit configured to accept a display instruction based on an operation input by a user;

a display control unit configured to display, as instructed by the display instruction, at least one image in a medical image display region, wherein, in a case where the accepted display instruction is a direct display instruction for the processed image and the accepted display instruction is not a direct display instruction for the at least one medical image used for the processing, the display control unit displays the processed image and the at least one medical image used for the processing, based on the information regarding the storage information stored by the storage unit, wherein, in a case where the accepted display instruction is not a display instruction for the processed image, the display control unit displays a medical image instructed by the accepted display instruction, and wherein the display control unit further divides the medical image display region into a plurality of partial regions based on information regarding the processing type, and to display the processed image and the at least one medical image used for the processing in accordance with a layout determined based on the related image information in the plurality of partial regions.

19. A method for an information processing apparatus, the method comprising:
acquiring, as a first acquiring, a processed image, wherein the acquired processed image was newly created by processing at least one medical image;
accepting a display instruction based on an operation input by a user;
storing related image information including information regarding a type of the processing and the at least one medical image used for the processing;
acquiring, as a second acquiring, the related image information; and
displaying, as instructed by the display instruction, at least one image in a medical image display region including a plurality of partial regions,
wherein, in a case where the accepted display instruction is a direct display instruction for the processed image and the accepted display instruction is not a direct display instruction for the at least one medical image used for the processing, displaying includes displaying, in the plurality of partial regions, the processed image and the at least one medical image used for the processing, based on the related image information acquired by the second acquiring, and
wherein displaying further includes dividing the medical image display region into the plurality of partial regions based on information regarding the processing type, and to display the processed image and the at least one medical image used for the processing in accordance with a layout determined based on the related image information in the plurality of partial regions.

20. An information processing system comprising:
a first acquiring unit configured to acquire a processed image, wherein the acquired processed image was newly created by processing at least one medical image;
an accepting unit configured to accept a display instruction based on an operation input by a user;
a storage unit configured to store related image information including information regarding a type of the processing and the at least one medical image used for the processing;
a second acquiring unit configured to acquire the related image information; and
a display control unit configured to display, as instructed by the display instruction, at least one image in a medical image display region including a plurality of partial regions,
wherein, in a case where the accepted display instruction is a direct display instruction for the processed image and the accepted display instruction is not a direct display instruction for the at least one medical image used for the processing, the display control unit displays, in the plurality of partial regions, the processed image and the at least one medical image used for the processing, based on the related image information acquired by the second acquiring unit, and
wherein the display control unit further divides the medical image display region into the plurality of partial regions based on information regarding the processing type and information describing the number of the at least one medical image used for the processing, and to display the processed image and the at least one medical image used for the processing in accordance with a layout determined based on the related image information in the plurality of partial regions.

21. An information processing apparatus comprising:
a first acquiring unit configured to acquire a processed image, wherein the acquired processed image was newly created by processing at least one medical image;
an accepting unit configured to accept a display instruction based on an operation input by a user;
a second acquiring unit configured to acquire information regarding a type of the processing and the at least one medical image used for the processing; and
a display control unit configured to display, as instructed by the display instruction, at least one image in a medical image display region including a plurality of partial regions,
wherein, in a case where the accepted display instruction is a direct display instruction for the processed image and the accepted display instruction is not a direct display instruction for the at least one medical image used for the processing, the display control unit displays, in the plurality of partial regions, the processed image and the at least one medical image used for the processing, based on the information acquired by the second acquiring unit, and
wherein, in a case where the processed image includes a plurality of temporal subtraction images generated by a plurality of combinations of a plurality of medical images of an identical object acquired at a plurality of time points, the display control unit displays, on an identical column or an identical row, a temporal subtraction image generated by using a medical image that is common in the plurality of combinations, and
wherein, in a case where past time point medical images at a past time point used for the plurality of combinations are not identical among the plurality of temporal subtraction images, the display control unit displays, on a different column or a different row, the temporal subtraction images generated by the past time point medical images not being identical at the past time point.

22. An information processing apparatus comprising:
a first acquiring unit configured to acquire a processed image, wherein the acquired processed image was created by processing at least one medical image;
an accepting unit configured to accept a display instruction based on an operation input by a user;
a storage unit configured to store related image information including information regarding a type of the processing and the at least one medical image used for the processing;
a second acquiring unit configured to acquire the related image information; and
a display control unit configured to display, as instructed by the display instruction, at least one image in a medical image display region including a plurality of partial regions,
wherein, in a case where the accepted display instruction is a direct display instruction for the processed image and the accepted display instruction is not a direct display instruction for the at least one medical image used for the processing, the display control unit displays, in the plurality of partial regions, the processed image and the at least one medical image used for the processing, based on the related image information acquired by the second acquiring unit, and
wherein, in a case where the processing type is a predetermined type, the display control unit further displays the processed image and the at least one medical image used for the processing in accordance with a predetermined layout.

23. The information processing apparatus according to claim 22, wherein the display control unit divides the medical image display region into the plurality of partial regions in a case where the type of the processing is a predetermined type, and further is configured to display the processed image and the at least one medical image used for the processing in the plurality of partial regions.

24. The information processing apparatus according to claim 22, wherein the processing type is temporal subtraction.

25. The information processing apparatus according to claim 22,
wherein the display control unit is configured to display a thumbnail of a medical image in a thumbnail display region, and
wherein the accepting unit is configured to accept a display instruction for a processed image corresponding to a corresponding thumbnail in response to a thumbnail operation input performed on the medical image thumbnail displayed in the thumbnail display region.

26. The information processing apparatus according to claim 25, wherein the display control unit is configured to display the processed image in a region specified based on the thumbnail operation input performed on the corresponding thumbnail.

27. An information processing apparatus comprising:
a first acquiring unit configured to acquire a temporal subtraction image, wherein the temporal subtraction image is generated by performing a difference process on a plurality of original images acquired by capturing at different times;
an accepting unit configured to accept a display instruction based on an operation input by a user;
a storage unit configured to store related image information including information regarding the plurality of original images used for the difference process;
a second acquiring unit configured to acquire the related image information; and
a display control unit configured to display at least one image, as instructed by the display instruction, in a medical image display region including a plurality of partial regions,
wherein, in a case where the accepted display instruction is a direct display instruction for the temporal subtraction image and the accepted display instruction is not a direct display instruction for the plurality of original images used for the difference process, the display control unit displays, in the plurality of partial regions in accordance with a predetermined layout, the temporal subtraction image and the plurality of original images, based on the related image information acquired by the second acquiring unit.

* * * * *